US012377036B2

United States Patent
Gianneschi et al.

(10) Patent No.: US 12,377,036 B2
(45) Date of Patent: Aug. 5, 2025

(54) MELANIN HAIR DYE WITH THICKENERS

(71) Applicant: Northwestern University, Evanston, IL (US)

(72) Inventors: Nathan C. Gianneschi, Wilmette, IL (US); Zofia Elzbieta Siwicka, Evanston, IL (US)

(73) Assignee: Northwestern University, Evanston, IL (US)

( * ) Notice: Subject to any disclaimer, the term of this patent is extended or adjusted under 35 U.S.C. 154(b) by 15 days.

(21) Appl. No.: 18/212,317

(22) Filed: Jun. 21, 2023

(65) Prior Publication Data

US 2023/0404890 A1 Dec. 21, 2023

Related U.S. Application Data

(60) Provisional application No. 63/353,891, filed on Jun. 21, 2022.

(51) Int. Cl.
*A61Q 5/10* (2006.01)
*A61K 8/04* (2006.01)
(Continued)

(52) U.S. Cl.
CPC ............... *A61K 8/65* (2013.01); *A61K 8/042* (2013.01); *A61K 8/66* (2013.01); *A61K 8/735* (2013.01);
(Continued)

(58) Field of Classification Search
CPC . A61K 8/65; A61K 8/042; A61K 8/66; A61K 8/735; A61K 8/737; A61K 2800/95; A61K 8/72; A61K 8/731; A61Q 5/10
(Continued)

(56) References Cited

U.S. PATENT DOCUMENTS 4,861,760 A 8/1989 Mazuel et al.
4,911,920 A 3/1990 Jani et al.
(Continued)

FOREIGN PATENT DOCUMENTS

CN 109172428 A * 1/2019
CN 109260071 1/2019
(Continued)

OTHER PUBLICATIONS

Battistella et al. (Oct. 2020) "Bioinspired Chemoenzymatic Route to Artificial Melanin for Hair Pigmentation," Chem. Mater. 32, 21, 9201-9210.
(Continued)

*Primary Examiner* — Eisa B Elhilo
(74) *Attorney, Agent, or Firm* — Leydig, Voit & Mayer, Ltd.

(57) ABSTRACT

Included herein are methods and materials for nontoxic, biocompatible, optionally metal-free, tunable, and long-lasting coloration of human hair. More particularly, provided herein are methods, and associated formulations, for efficient formation and deposition of synthetic melanin to human hair, thereby coloration of hair, whereby the hair treatment formulation is viscous enough for treatment of hair without substantially loss of the formulation which further allows an easier application process that includes exposing the hair to the treatment formulation for an extended amount of time. For example, the hair treatment formulation, or viscous solution, can be applied and left on the hair, such as if it were a cream or gel, without requiring soaking the hair in a bath. Different colors can be achieved by tuning reaction conditions such as temperature and solution phase composition. These methods, and associated materials, can be used in salons and at home, for example,
(Continued)

without degradation of the resulting colored hair and safety of the user of the present materials and methods.

39 Claims, 3 Drawing Sheets

(51) Int. Cl.
    *A61K 8/65*     (2006.01)
    *A61K 8/66*     (2006.01)
    *A61K 8/73*     (2006.01)

(52) U.S. Cl.
    CPC ............... *A61K 8/737* (2013.01); *A61Q 5/10* (2013.01); *A61K 2800/95* (2013.01)

(58) Field of Classification Search
    USPC .......................................................... 8/405
    See application file for complete search history.

(56) References Cited

U.S. PATENT DOCUMENTS

| | | |
|---|---|---|
| 5,212,162 A | 5/1993 | Missel et al. |
| 5,368,610 A | 11/1994 | Chan et al. |
| 5,403,841 A | 4/1995 | Lang et al. |
| 5,441,542 A | 8/1995 | Prota et al. |
| 5,547,658 A | 8/1996 | Hansenne et al. |
| 5,628,799 A | 5/1997 | Wenke et al. |
| 8,067,044 B2 | 11/2011 | Henry et al. |
| 8,586,090 B2 | 11/2013 | Dadachova et al. |
| 11,045,493 B2 | 6/2021 | Gianneschi et al. |
| 2008/0052841 A1 | 3/2008 | Cohen et al. |
| 2009/0178209 A1 | 7/2009 | Koike et al. |
| 2011/0020252 A1 | 1/2011 | Shantha et al. |
| 2011/0236325 A1 | 9/2011 | Mitchell et al. |
| 2013/0078205 A1 | 3/2013 | Dayan et al. |
| 2013/0177616 A1 | 7/2013 | de Olivera et al. |
| 2014/0044789 A1 | 2/2014 | Dadachova et al. |
| 2015/0093342 A1 | 4/2015 | Domloge et al. |
| 2020/0113934 A1 | 4/2020 | Gianneschi et al. |
| 2021/0393673 A1 | 12/2021 | Gianneschi et al. |
| 2022/0332670 A1 | 10/2022 | Zhou et al. |

FOREIGN PATENT DOCUMENTS

| | | | | |
|---|---|---|---|---|
| CN | 109846742 A | * | 6/2019 | ............... A61Q 5/10 |
| CN | 114028252 A | * | 2/2022 | ............... A61Q 5/10 |
| CN | 114159351 A | * | 3/2022 | ............... A61Q 5/10 |
| CN | 115517991 A | * | 12/2022 | ............... A61Q 5/10 |
| EP | 1301165 | | 4/2003 | |
| EP | 2873412 | | 5/2015 | |
| KR | 10-2016- 0072590 | | 6/2016 | |
| WO | WO 1993/005759 | | 4/1993 | |
| WO | WO 2009/003037 | | 12/2008 | |
| WO | WO 2017/064672 | | 4/2017 | |
| WO | WO 2018/013609 | | 1/2018 | |
| WO | WO 2021/021350 | | 2/2021 | |
| WO | WO 2021/087076 | | 5/2021 | |
| WO | WO 2021/096692 | | 5/2021 | |
| WO | WO 2022/140532 | | 6/2022 | |
| WO | WO 2022/232356 | | 11/2022 | |
| WO | WO 2023/150205 | | 8/2023 | |

OTHER PUBLICATIONS

"NanoComposix's Guide to Dynamic Light Scattering Measurement and Analysis" [dated Feb. 2015 (version 1.4), published by nanoComposix of San Diego, CA, and available at nanoComposix_ Guidelines_for_DLS_Measurements_and_Analysis (last accessed Jun. 26, 2019), pp. 1-8.
Abcam Flow cytometric analysis of cell cycle with propidium iodide DNA staining. https://www.abcam.com/protocols/flow-cytometric-analysis-of-cell-cycle-with-propidium-iodide-dna-staining.
Akiladevi et al. (2010) "Ethosomes—A noninvasive approach for transdermal drug delivery," Int J Current Pharm Res 2(4): 1-4.
Ali et al. (Oct. 2018) "Aqueous MEA and Ammonia Sorption-Induced Damage in Keratin Fibers," ACS Omega, 3 (10), 14173-14180.
Alikhan et al. (2011) "Vitiligo: a comprehensive overview: part I. Introduction, epidemiology, quality of life, diagnosis, differential diagnosis, associations, histopathology, etiology, and work-up," J. Am. Acad. Dermatol. 65(3): 473-491.
Alipour (May 2020) "Comments on: Hair dye and chemical straightener use and breast cancer risk in a large US population of black and white women," International Journal of Cancer, 146 (9), 2651-2651.
Al-Muhammed et al. (1996) "In-vivo studies on dexamethasone sodium phosphate liposomes," J. Microencapsul. 13(3): 293-306.
Ando et al. (2007) "Approaches to identify inhibitors of melanin biosynthesis via the quality control of tyrosinase," J. Invest. Dermatol. 127(4): 751-761.
Ando et al. (2012) "Melanosomes are transferred from melanocytes to keratinocytes through the processes of packaging, release, uptake, and dispersion," J. Invest. Dermatol. 132(4): 1222-1229.
Apte et al. (2013) "Psychrotrophic yeast Yarrowia lipolytica NCYC 789 mediates the synthesis of antimicrobial silver nanoparticles via cell-associated melanin," AMB Express 3:32, pp. 1-8.
Au et al. (2011) "Polypyrrole Nanoparticles: A Potential Optical Coherence Tomography Contrast Agent for Cancer Imaging," Adv Mater, 23 (48), 5792-5795.
Ba et al. (2017) "Recent developments in the use of tyrosinase and laccase in environmental applications," Crit Rev Biotechnol, 37 (7), 819-832.
Bailey et al. (2014) "Comparison of damage to human hair fibers caused by monoethanolamine- and ammonia-based hair colorants," J Cosmet Sci, 65 (1), 1-9.
Bardestani et al. (2019) "Experimental methods in chemical engineering: specific surface area and pore size distribution measurements— BET, BJH, and DFT," The Canadian Journal of Chemical Engineering 97(11): 2781-2791.
Battistella et al. (Apr. 2020) "Mimicking Natural Human Hair Pigmentation with Synthetic Melanin," ACS Cent. Sci. 6(7): 1179-1188.
Beltran-Garcia et al. (2014) "Singlet Molecular Oxygen Generation by Light-Activated DHN-Melanin of the Fungal Pathogen Mycosphaerella fijiensis in Black Sigatoka Disease of Bananas," PLOS ONE 9(3): e91616, pp. 1-15.
Berge et al. (1977) "Pharmaceutical Salts," Journal of Pharmaceutical Sciences 66(1): 1-19.
Bernard et al. (publicly available 2016) "Consumption of hair dye products by the French women population: Usage pattern and exposure assessment," Food and Chemical Toxicology 88: 123-132.
Bikle et al. (2012) "Calcium Regulation of Keratinocyte Differentiation," Expert Rev. Endocrinol. Metab. 7(4): 461-472.
Borowska et al. (2015) "Metals in cosmetics: implications for human health," J Appl Toxicol 35(6): 551-572.
Boulton et al. (2001) "Retinal Photodamage," J. Photochem. Photobiol. B: Biol. 64(2-3): 144-161.
Brenner et al. (2008) "The protective role of melanin against UV damage in human skin," Photochem Photobiol, 84 (3), 539-549.
Byers et al. (2003) "Role of Cytoplasmic Dynein in Perinuclear Aggregation of Phagocytosed Melanosomes and Supranuclear Melanin Cap Formation in Human Keratinocytes," J. Invest. Dermatol. 121(4): 813-820.
Byers et al. (2007) "Requirement of dynactin p150$^{Glued}$ subunit for the functional integrity of the keratinocyte microparasol," J. Investi. Dermatol. 127(7): 1736-1744.
Cao et al. (2017) "A novel method for non-destructive determination of hair photo-induced damage based on multispectral imaging technology," Sci Rep-Uk, 7.
Cao et al. (Jul. 2020) "Selenomelanin: An Abiotic Selenium Analogue of Pheomelanin," Journal of the American Chemical Society, vol. 142, Issue 29, p. 12802-12810.
Cecchini et al. (May 2017) "Modeling Fungal Melanin Buildup: Biomimetic Polymerization of 1,8-Dihydroxynaphthalene Mapped by Mass Spectrometry," Chem. Eur. J. 23: 8092-8098.

(56) References Cited

OTHER PUBLICATIONS

Chen et al. (2014) "Engineering fluorescent poly(dopamine) capsules," Langmuir 30(10): 2921-2925.
Chen et al. (Nov. 2016) "Nanoscale Polydopamine (PDA) Meets Π-529 Interactions: An Interface-Directed Coassembly Approach for Mesoporous Nanoparticles," Langmuir 32(46): 12119-12128.
Chonn et al. (1995) "Recent advances in liposomal drug-delivery systems," Curr. Opin. Biotechnol. 6(6): 698-708.
Chung (Sep. 2016) "Azo dyes and human health: A review," J Environ Sci Health C Environ Carcinog Ecotoxicol Rev 34: 233-261.
Coenraads et al. (Oct. 2018) "The Allergy Alert Test: Introduction of a Protocol Suitable to Provide an Alert Signal in p-Phenylenediamine-Allergic Hair Dye Users," Dermatitis, 29(5), 231-232.
Cordero et al. (Feb. 2020) "Melanin." Curr Biol 30 (4), R142-R143.
Dadachova et al. (2007) "Ionizing Radiation Changes the Electronic Properties of Melanin and Enhances the Growth of Melanized Fungi," Plos One 2(5): e457, pp. 1-13.
Dadachova et al. (2008) "Ionizing Radiation: How Fungi Cope, Adapt, and Exploit with the Help of Melanin," Curr. Opin. Microbiol. 11(6): 525-531.
Dadachova et al. (2008) "The radioprotective properties of fungal melanin are a function of its chemical composition, stable radical presence and spatial arrangement," Pigment Cell Melanoma Res 21(2): 192-199.
D'Alba et al. (Sep. 2018) "Melanosomes: Biogenesis, Properties, and Evolution of an Ancient Organelle," Physiol. Rev. 99: 1-19.
Dell'Angelica et al. (2000) "Lysosome-related organelles," FASEB J. 14(10): 1265-1278.
d'ischia et al. (2014) "Polydopamine and eumelanin: from structure-property relationships to a unified tailoring strategy," Acc. Chem. Res. 47, (12), 3541-50.
d'Ischia et al. (2015) "Melanins and Melanogenesis: from Pigment Cells to Human Health and Technological Applications," Pigm. Cell Melanoma Res. 28(5): 520-544.
D'mello et al. (2016) "Signaling Pathways in Melanogenesis," Int J Mol Sci, 17 (7).
Dolgova et al. (2016) "Distribution of selenium in zebrafish larvae after exposure to organic and inorganic selenium forms," Metallomics, Issue 3, p. 305-312.
Dong et al. (Oct. 2019) "Melanin-mimetic multicolor and low-toxicity hair dye," Rsc Adv, 9 (58), 33617-33624.
Draelos (2006) "Sunscreens and hair photoprotection," Dermatologic Clinics, 24 (1), 81-84.
Durante et al. (2011) Physical basis of radiation protection in space travel. Rev. Mod. Phys. 83, (4), 1245-1281.
Eberle et al. (Dec. 2019) "Hair dye and chemical straightener use and breast cancer risk in a large US population of black and white women," International Journal of Cancer, 147, 383-391.
Eisenman et al. (2005) "Microstructure of Cell Wall-Associated Melanin in the Human Pathogenic Fungus Cryptococcus neoformans," Biochemistry 44(10): 3683-3693.
Etebari et al. (2015) "Evaluation of protective effect of amifostine on dacarbazine induced genotoxicity" Res Pharm Sci 10, (1), 68-74.
Eyles et al. (1997) "Oral Delivery and Fate of Poly(lactic acid) Microsphere- encapsulated Interferon in Rats," J. Pharm. Pharmacol. 49(7): 669-674.
Fan et al. (2014) "Transferring biomarker into molecular probe: melanin nanoparticle as a naturally active platform for multimodality imaging," J. Am. Chem. Soc. 136(43): 15185-15194.
Faria et al. (2007) "The biotechnological potential of mushroom tyrosinases," Food Technol Biotech, 45 (3), 287-294.
Ferguson et al. (Apr. 2019) "Addressing the conundrums of p-phenylenediamine hair dye allergy by applying Friedmann's principles of contact sensitization," Contact Dermatitis, 80 (4), 234-237.
Fernandez-Llamosas et al. (2017) "Speeding up bioproduction of selenium nanoparticles by using Vibrio natriegens as microbial factory," Sci Rep, 7, (1), 16046.
Foote et al. (1996) Active Oxygen in Chemistry.
Gago-Dominguez et al. (2001) "Use of permanent hair dyes and bladder-cancer risk," Int J Cancer 91(4): 575-579.
Gao (1995) "Controlled Release of a Contraceptive Steroid from Biodegradable and Injectable Gel Formulations: In Vitro Evaluation," Pharm. Res. 12(6): 857-863.
Gao et al. (2013) "Mussel-Inspired Synthesis of Polydopamine-Functionalized Graphene Hydrogel as Reusable Adsorbents for Water Purification," ACS Applied Materials & Interfaces 5(2): 425-432.
Gao et al. (Jun. 2019) "Rapid preparation of polydopamine coating as a multifunctional hair dye," Rsc Adv, 9 (35), 20492-20496.
Ghiani et al. (2008) "Characterization of human hair melanin and its degradation products by means of magnetic resonance techniques," Magn Reson Chem 46(5): 471-479.
Glass et al. (2012) "Direct chemical evidence for eumelanin pigment from the Jurassic period" Proc. Natl. Acad. Sci. U. S. A. 109, (26), 10218-23.
Guerra-Tapia et al. (2014) "Hair cosmetics: dyes," Actas Dermo-Sifiliograficas 105(9): 833-839.
Guo et al. (Mar. 2020) "In vivo photothermal inhibition of methicillin-resistant Staphylococcus aureus infection by in situ templated formulation of pathogen- targeting phototheranostics," Nanoscale, 12 (14), 7651-7659.
Haining et al. (Mar. 2017) "Neuromelanin, One of the Most Overlooked Molecules in Modern Medicine, is not a Spectator," Neural Regen. Res. 12(3): 372-375.
Hall et al. (Jul. 2016) "Protection against Radiotherapy-Induced Toxicity," Antioxidants (Basel) 5(3): 22, pp. 1-18.
Han et al. (Apr. 2015) "Dual-Stage-Light-Guided Tumor Inhibition by Mitochondria-Targeted Photodynamic Therapy," Adv. Funct. Mater. 25(20): 2961-2971.
Han et al. (Apr. 2018) "P-Phenylenediamine Hair Dye Allergy and Its Clinical Characteristics," Ann Dermatol, 30 (3), 316-321.
Harrison et al. (2003) "Hair colouring, permanent styling and hair structure," J Cosmet Dermatol 2(3-4): 180-185.
Hasegawa et al. (2015) "Health effects of radiation and other health problems in the aftermath of nuclear accidents, with an emphasis on Fukushima." Lancet 386, (9992), 479-488.
Haveli et al. (2012) "Hair Fiber as a Nanoreactor in Controlled Synthesis of Fluorescent Gold Nanoparticles," Nano Lett 12(12): 6212-6217.
Hennessy et al. (2005) "Eumelanin and Pheomelanin Concentrations in Human Epidermis before and after UVB Irradiation," Pigm. Cell Res. 18(3): 220-223.
Herrling et al. (2008) "The role of melanin as protector against free radicals in skin and its role as free radical indicator in hair," Spectrochim Acta A, 69 (5), 1429-1435.
Hink et al. (2006) "Hair-dye allergy: a coloured case," Eur J Pediatr, 165 (3), 195-6.
Hong et al. (2004) "Binding of Metal Ions to Melanin and Their Effects on the Aerobic Reactivity," Photochem. Photobiol. 80(3): 477-481.
Hong et al. (2007) "Current Understanding of the Binding Sites, Capacity, Affinity, and Biological Significance of Metals in Melanin," J. Phys. Chem. B 111(28): 7938-7947.
Huang et al. (2017) "Mimicking Melanosomes: Polydopamine Nanoparticles as Artificial Microparasols," and Suppl. Info., ACS Cent. Sci. (Jun. 2017) 3(6): 564-569 (22 pp. total).
Huang et al. (2018) "Recent Advances and Progress on Melanin-like Materials and Their Biomedical Applications," Biomacromolecules 19: 1858-1868.
Hunt et al. (1995) "Eumelanin and phaeomelanin contents of human epidermis and cultured melanocytes," Pigment Cell Res. 8(4): 202-208.
Im et al. (2017) "Metal-Chelation-Assisted Deposition of Polydopamine on Human Hair: A Ready-to-Use Eumelanin-Based Hair Dyeing Methodology," Acs Biomater Sci Eng, 3 (4), 628-636.
International Preliminary Report on Patentability, dated Jan. 24, 2019, corresponding to International Application No. PCT/US2017/041596 (filed Jul. 11, 2017), 10 pp.
International Search Report and Written Opinion, dated Apr. 14, 2023, corresponding to International Application No. PCT/US2023/012182, 10 pp.

(56) References Cited

OTHER PUBLICATIONS

International Search Report and Written Opinion, dated Feb. 26, 2021, corresponding to International Patent Application No. PCT/US2020/039769, 13 pages.
International Search Report and Written Opinion, dated Jan. 26, 2021, corresponding to International Patent Application No. PCT/US2020/057902, 11 pages.
International Search Report and Written Opinion, dated Jan. 30, 2018, corresponding to International Application No. PCT/US2017/041596 (filed Jul. 11, 2017), 12pp.
International Search Report and Written Opinion, dated Mar. 4, 2021, corresponding to International Application No. PCT/US2020/057939, (from which the present application claims priority,) 14 pp.
Ito (1989) "Optimization of conditions for preparing synthetic pheomelanin." Pigment Cell Res 2, (1), 53-6.
Ito et al. (1980) "Co-polymerization of dopa and cysteinyldopa in melanogenesis in vitro," Experientia 36(7): 822-823.
Ito et al. (1985) "Microanalysis of eumelanin and pheomelanin in hair and melanomas by chemical degradation and liquid chromatography," Anal. Biochem. 144(2): 527-536.
Ito et al. (2003) "Quantitative analysis of eumelanin and pheomelanin in humans, mice, and other animals: a comparative review," Pigment Cell Res. 16(5): 523-531.
Ito et al. (2008) "Chemistry of Mixed Melanogenesis-Pivotal Roles of Dopaquinone," Photochem. Photobiol. 84(3): 582-592.
Iwamoto et al. (1999) "Different cell cycle mechanisms between UV-induced and X-ray-induced apoptosis in WiDr colorectal carcinoma cells," Apoptosis 4(1): 59-66.
Jablonski et al. (2010) "Human skin pigmentation as an adaptation to UV radiation," P Natl Acad Sci USA, 107, 8962-8968.
Jeon et al. (2016) "Dihydroxynaphthalene-based mimicry of fungal melanogenesis for multifunctional coatings," Microb Biotechnol, 9 (3), 305-15.
Ji et al. (2013) "The Ethnic Differences of the Damage of Hair and Integral Hair Lipid after Ultra Violet Radiation," Annals of Dermatology, 25 (1), 54-60.
Ji et al. (2014) "Dynamic diselenide bonds: exchange reaction induced by visible light without catalysis," Angew. Chem. Int. Ed. 53, (26), 6781-5.
Jin et al. (2012) "Genome-wide association analyses identify 13 new susceptibility loci for generalized vitiligo," Nat. Genet. 44(6): 676-680.
Johnson (Jul. 2017) Safety Assessment of Ammonia and Ammonium Hydroxide as Used in Cosmetics, Cosmetic Ingredient Review, 42 pages.
Ju et al. (2011) "Bioinspired polymerization of dopamine to generate melanin-like nanoparticles having an excellent free-radical-scavenging property," Biomacromolecules 12(3): 625-632.
Ju et al. (2013) "Bio-Inspired, Melanin-Like Nanoparticles as a Highly Efficient Contrast Agent for $T_1$-Weighted Magnetic Resonance Imaging," Biomacromolecules 14(10): 3491-3497.
Ju et al. (publicly available Sep. 2014) "Bio-inspired Development of a Dual-Mode Nanoprobe for MRI and Raman Imaging," Small (Jan. 2015) 11(1): 84-89.
Kang et al. (2018) "Reverse Engineering To Characterize Redox Properties: Revealing Melanin's Redox Activity through Mediated Electrochemical Probing," Chem. Mater. 30: 5814-5826.
Kasraee et al. (2012) "Ebselen is a new skin depigmenting agent that inhibits melanin biosynthesis and melanosomal transfer," Exp. Dermatol. 21: 19-24.
Kawamura et al. (2016) "Full-Color Biomimetic Photonic Materials with Iridescent and Non-Iridescent Structural Colors." Sci Rep 6, 33984.
Keogh et al. (1965) "Rate of Greying of Human Hair," Nature 207: 877-878.
Kim et al. (2010) "Biomimetic Approach to Confer Redox Activity to Thin Chitosan Films," Adv. Funct. Mater. 20(16): 2683-2694.
Kim et al. (2011) "Development of a high-content screening method for chemicals modulating DNA damage response," J. Biomol. Screen. 16(2): 259-265.
Kim et al. (2016) "The use of personal hair dye and its implications for human health," Environ Int, 89-90, 222-227.
Kim et al. (Jun. 2018) "Enzymatic film formation of nature-derived phenolic amines," Nanoscale, 10 (28), 13351-13355.
Kim et al. (Oct. 2017) "Spectroelectrochemical Reverse Engineering Demonstrates That Melanin's Redox and Radical Scavenging Activities Are Linked," Biomacromolecules 18(12): 4084-4098.
Kobayashi et al. (1993) "Melanin Reduces Ultraviolet-Induced DNA Damage Formation and Killing Rate in Cultured Human Melanoma Cells," J. Invest. Dermatol. 101(5): 685-689.
Kobayashi et al. (1998) "Supranuclear melanin caps reduce ultraviolet induced DNA photoproducts in human epidermis," J. Invest. Dermatol. 110(5): 806-810.
Korner et al. (1982) "Mammalian tyrosinase catalyzes three reactions in the biosynthesis of melanin," Science 217(4565): 1163-1165.
Kryukov et al. (2003) "Characterization of mammalian selenoproteomes," Science, 300, (5624), 1439-43.
Kumar (2005) "Exploratory analysis of global cosmetic industry: major players, technology and market trends," Technovation 25(11): 1263-1272.
Kunwar et al. (2010) "In vivo radioprotection studies of 3,3'-diselenodipropionic acid, a selenocystine derivative," Free Radic Biol Med 2010, 48 (3), 399-410.
Kunwar et al. (2011) "Anti-apoptotic, anti-inflammatory, and immunomodulatory activities of 3,3'-diselenodipropionic acid in mice exposed to whole body gamma- radiation," Arch Toxicol 2011, 85 (11), 1395-405.
Lai et al. (Jan. 2018) "Structure and Function of Human Tyrosinase and Tyrosinase-Related Proteins," Chem-Eur J, 24 (1), 47-55.
Lampel et al. (Jun. 2017) "Polymeric Peptide Pigments with Sequence-Encoded Properties," Science 356(6342): 1064-1068.
Lee (2009) "Photoaggravation of hair aging," Int J Trichology, 1 (2), 94-9.
Lee et al. (2007) "A reversible wet/dry adhesive inspired by mussels and geckos." Nature 448, (7151), 338-41.
Lee et al. (2007) "Mussel-Inspired Surface Chemistry for Multifunctional Coatings," Science 318(5849): 426-430.
Lee et al. (Feb. 2015) "Retinal development in albinism: a prospective study using optical coherence tomography in infants and young children," Lancet. 385(Suppl 1): p. S14.
Lemaster et al. (Jan. 2019) "Gadolinium Doping Enhances the Photoacoustic Signal of Synthetic Melanin Nanoparticles: A Dual Modality Contrast Agent for Stem Cell Imaging," Chem. Mater. 31(1): 251-259.
Lent et al. (2017) "Acute and subacute oral toxicity of periodate salts in rats," Regul Toxicol Pharmacol 83: 23-37.
Li et al. (2016) "Polycatechol Nanoparticle MRI Contrast Agents," Small (Feb. 2016) 12(5): 668-677.
Liebscher et al. (2013) "Structure of polydopamine: a never-ending story?" Langmuir 29(33): 10539-10548.
Lin et al. (publicly available Mar. 2016) "Multimodal-Imaging-Guided Cancer Phototherapy by Versatile Biomimetic Theranostics with UV and γ-Irradiation Protection," Adv Mater (May 2016) 28(17): 3273-3279.
Liu et al. (2003) "Comparison of the Structural and Physical Properties of Human Hair Eumelanin Following Enzymatic or Acid/Base Extraction." Pigment Cell Res. 16, (4), 355-365.
Liu et al. (2004) "Ion-Exchange and Adsorption of Fe(III) by Sepia Melanin," Pigm. Cell Res. 17(3): 262-269.
Liu et al. (2013) "Mussel-Inspired Polydopamine: a Biocompatible and Ultrastable Coating for Nanoparticles in vivo," ACS Nano 7(10): 9384-9395.
Liu et al. (2014) "Polydopamine and its derivative materials: synthesis and promising applications in energy, environmental, and biomedical fields," Chem. Rev. 114(9): 5057-5115.
Liu et al. (2019) "Role of Polydopamine's Redox-activity on Its Pro-oxidant, Radical-scavenging, and Antimicrobial Activities," Acta Biomater. 88: 181-196.
Liu et al. (publicly available Dec. 2016) "Comprehensive Insights into the Multi-Antioxidative Mechanisms of Melanin Nanoparticles and Their Application To Protect Brain from Injury in Ischemic Stroke," J. Am. Chem. Soc. (Jan. 2017) 139(2): 856-862.

(56) References Cited

OTHER PUBLICATIONS

Luo et al. (Apr. 2018) "Multifunctional Graphene Hair Dye," Chem-US 4: 784-794.
Lusic et al. (2013) "X-ray-computed tomography contrast agents" Chem. Rev. 113, (3), 1641-1666.
Ma et al. (2010) "Selenium-containing block copolymers and their oxidation-responsive aggregates," Polym. Chem. 1, 1609-1614.
Macleod et al. (2015) "PEGylated N-Heterocyclic Carbene Anchors Designed To Stabilize Gold Nanoparticles in Biologically Relevant Media," J. Am. Chem. Soc. 137(25): 7974-7977.
Maia et al. (2013) "Key ornamental innovations facilitate diversification in an avian radiation." Proc. Natl. Acad. Sci. U. S. A. 110, (26), 10687-10692.
Maia et al. (Jul. 2019) "pavo 2: New tools for the spectral and spatial analysis of colour in r," Methods Ecol Evol, 10 (7), 1097-1107.
Manini et al. (2018) "Characterization and Fate of Hydrogen-Bonded Free-Radical Intermediates and Their Coupling Products from the Hydrogen Atom Transfer Agent 1,8-Naphthalenediol," ACS Omega 3: 3918-3927.
Manini et al. (2019) "A Robust Fungal Allomelanin Mimic: An Antioxidant and Potent pi-Electron Donor with Free-Radical Properties that can be Tuned by Ionic Liquids," Chempluschem 84(9): 1331-1337.
Manini et al. (2020) "Synthetic mycomelanin thin films as emergent bio-inspired interfaces controlling the fate of embryonic stem cells," J Mater Chem B 8(20): 4412-4418.
Mariotti et al. (May 2019) "Utilization of selenocysteine in early-branching fungal phyla," Nat Microbiol, 4, (5), 759-765.
Marks et al. (2001) "The melanosome: membrane dynamics in black and white," Nat. Rev. Mol. Cell Biol. 2: 738-748 (11 pages).
Martinez et al. (Oct. 2019) "Production of Melanins With Recombinant Microorganisms" Front Bioeng Biotechnol 7, 285.
Martyn-Simmons et al. (2006) "Adult T-cell leukaemia/lymphoma masquerading as a hair dye allergy," Br J Dermatol, 154 (1), 196-7.
Mbonyiryivuze et al. (2015) "Fourier Transform Infrared Spectroscopy for Sepia Melanin" Phys. Mater. Chem. 3, (2), 25-29.
McFadden et al. (2007) "Allergy to hair dye—Its incidence is rising, as more and younger people dye their hair," Brit Med J 334: 220-220.
Meredith et al. (2006) "The physical and chemical properties of eumelanin," Pigment Cell Res. 19(6): 572-594.
Mironenko et al. (2000) "Intraspecific variation in gamma-radiation resistance and genomic structure in the filamentous fungus Alternaria alternata: a case study of strains inhabiting Chernobyl reactor No. 4," Ecotoxicol Environ Saf 45(2): 177-187.
Montefiori et al. (1990) "Inhibition of Human Immunodeficiency Virus Type 1 Replication and Cytopathicity by Synthetic Soluble Catecholamine Melanins In Vitro," Biochem. And Biophys. Res. Comm. 1990, 168 (1), 200-205.
Montoliu et al. (2014) "Increasing the complexity: new genes and new types of albinism," Pigment Cell Melanoma Res. 27(1): 11-18.
Morel et al. (2011) "Current Trends in the Chemistry of Permanent Hair Dyeing," Chem Rev 111(4): 2537-2561.
Mostert et al. (Mar. 2018) "The photoreactive free radical in eumelanin," Science Advances 4(3).
Mouret et al. (2006) "Cyclobutane pyrimidine dimers are predominant DNA lesions in whole human skin exposed to UVA radiation," Proc. Natl. Acad. Sci. 103(37): 13765-13770.
Mutsaers (2004) "The mesothelial cell," Int. J. Biochem. Cell Biol. 36(1): 9-16.
Nambiar et al. (2012) "Polymer-composite materials for radiation protection," ACS Appl Mater Interfaces 4(11): 5717-5726.
Napolitano et al. (2013) "Red Hair Benzothiazines and Benzothiazoles: Mutation-Inspired Chemistry in the Quest for Functionality," Acc. Chem. Res. 46(2): 519-528.
Ni et al. (Jul. 2020) "Chemoenzymatic elaboration of the Raper—Mason pathway unravels the structural diversity within eumelanin pigments," Chem Sci, 11, 7836-7841.

Nishimura et al. (2005) "Mechanisms of hair graying: Incomplete melanocyte stem cell maintenance in the niche," Science 307(5710): 720-724.
Nogueira et al. (2006) "About photo-damage of human hair," Photoch Photobio Sci, 5 (2), 165-169.
Nogueira et al. (2007) "Photo yellowing of human hair," J Photoch Photobio B, 88 (2-3), 119-125.
Nosanchuk et al. (2003) "The Contribution of Melanin to Microbial Pathogenesis," Cell. Microbiol. 5(4): 203-223.
Nosanchuk et al. (2015) "Fungal Melanin: What do We Know About Structure?" Front. Microbiol. 6, 1463: pp. 1-7.
Ochs et al. (2011) "Dopamine-mediated continuous assembly of biodegradable capsules," Chem. Mater. 23(13): 3141-3143.
Orlow (1995) "Melanosomes are specialized members of the lysosomal lineage of organelles," J. Invest. Dermatol. 105(1): 3-7.
Pacelli et al. (publicly available Jan. 2017) "Melanin is Effective in Protecting Fast and Slow Growing Fungi from Various Types of Ionizing Radiation," Environ. Microbiol. (Apr. 2017) 19(4): 1612-1624.
Panzella et al. (2013) "Atypical structural and pi-electron features of a melanin polymer that lead to superior free-radical-scavenging properties." Angew. Chem. Int. Ed. 2013, 52, (48), 12684-7.
Panzella et al. (Jun. 2018) "The Late Stages of Melanogenesis: Exploring the Chemical Facets and the Application Opportunities," Int J Mol Sci, 19 (6).
Park et al. (publicly available Nov. 2016) "Novel Neuroprotective Effects of Melanin-Concentrating Hormone in Parkinson's Disease," Mol. Neurobiol. (Dec. 2017) 54: 7706-7721.
Patel et al. (2013) "Trends in use of hair dye: a cross-sectional study," Int J Trichology 5(3): 140-143, 9 pages.
Pezzella et al. (1997) "Identification of Partially Degraded Oligomers of 5, 6-Dihydroxyindole-2-carboxylic Acid in Sepia Melanin by Matrix-assisted Laser Desorption/Ionization Mass Spectrometry," Rapid Commun. Mass Spectrom. 11(4): 368-372.
Pihet et al. (2009) "Melanin is an Essential Component for the Integrity of the Cell Wall of Aspergillus Fumigatus Conidia," BMC Microbiol. 9: 177, pp. 1-11.
Premi et al. (2015) "Chemiexcitation of melanin derivatives induces DNA photoproducts long after UV exposure" Science 347, (6224), 842-847.
Prota, G. (2000) "Melanins, melanogenesis and melanocytes: looking at their functional significance from the chemist's viewpoint" Pigment Cell Res 13 (4), 283-93.
Pyo et al. (publicly available Apr. 2016) "Artificial pheomelanin nanoparticles and their photo-sensitization properties," J Photochem Photobiol B (Jul. 2016) 160: 330-335.
QSTIO (1989) Am. J Hasp. Pharm. 46: 1576-1587.
Rao (1995) "Recent developments of collagen-based materials for medical applications and drug delivery systems," J Biomater Sci. Polym. Ed 7(7): 623-645.
Raposo et al. (2007) "Melanosomes—dark organelles enlighten endosomal membrane transport," Nat. Rev. Mol. Cell Biol. 8(10): 786-797.
Ren et al. (2013) "High level production of tyrosinase in recombinant *Escherichia coli*" BMC Biotechnol 13, 18.
Ricci et al. (2016) "Drug-induced hair colour changes," Eur J Dermatol 26(6): 531-536.
Richena et al. (2015) "Effect of photodamage on the outermost cuticle layer of human hair," J Photoch Photobio B, 153, 296-304.
Richena et al. (2016) "Morphological degradation of human hair cuticle due to simulated sunlight irradiation and washing," J Photoch Photobio B, 161, 430-440.
Riley (1997) "Melanin," Int J Biochem Cell B 29(11): 1235-1239.
Robbins (2012) "Bleaching and Oxidation of Human Hair," In Chemical and Physical Behavior of Human Hair, Springer Berlin Heidelberg: Berlin, Heidelberg, pp. 263-328.
Robertson et al. (2012) "Adaptation of the Black Yeast Wangiella dermatitidis to Ionizing Radiation: Molecular and Cellular Mechanisms," Plos One 7(11): e48674, pp. 1-18.
Rosenfeld et al. (2017) "Selenium (IV,VI) reduction and tolerance by fungi in an oxic environment," Geobiology, 15, (3), 441-452.

(56) References Cited

OTHER PUBLICATIONS

Rouse et al. (2007) "Effects of Mechanical Flexion on the Penetration of Fullerene Amino Acid-Derivatized Peptide Nanoparticles through Skin," Nano Letters 7(1): 155-160.

Ryu et al. (Mar. 2018) "Polydopamine Surface Chemistry: A Decade of Discovery," ACS Appl Mater Interfaces 10(9): 7523-7540.

Santos Nogueira et al. (2004) "Hair color changes and protein damage caused by ultraviolet radiation," J Photochem Photobiol B, 74 (2-3), 109-17.

Schmaler-Ripcke et al. (2009) "Production of Pyomelanin, a Second Type of Melanin, via the Tyrosine Degradation Pathway in Aspergillus fumigatus," Appl. Environ. Microbiol. 75(2): 493-503.

Schomburg et al. (2004) "Selenium and selenoproteins in mammals: extraordinary, essential, enigmatic," Cell. Mol. Life Sci. 61, (16), 1988-1995.

Schweitzer et al. (2009) "Physico-Chemical Evaluation of Rationally Designed Melanins as Novel Nature-Inspired Radioprotectors," PLOS ONE 4(9): e7229, pp. 1-8.

Schweitzer et al. (2010) "Melanin-Covered Nanoparticles for Protection of Bone Marrow during Radiation Therapy of Cancer," Int. J. Radiat. Oncol. Biol. Phys. 78(5): 1494-1502.

Scott et al. (2002) "Filopodia are conduits for melanosome transfer to keratinocytes," J. Cell Sci. 115(7): 1441-1451.

Seagle et al. (2005) "Melanin photoprotection in the human retinal pigment epithelium and its correlation with light-induced cell apoptosis," Proceedings of the National Academy of Sciences of the United States of America 102(25): 8978-8983.

Seagle et al. (2005) "Time-Resolved Detection of Melanin Free Radicals Quenching Reactive Oxygen Species," J. Am. Chem. Soc. 127(32): 11220-11221.

Sealy et al. (1982) "Eumelanins and pheomelanins: characterization by electron spin resonance spectroscopy," Science 217(4559): 545-547.

Seo et al. (2003) "Mushroom tyrosinase: Recent prospects," J Agr Food Chem, 51 (10), 2837-2853.

Seo et al. (2012) "Hydrogen peroxide and monoethanolamine are the key causative ingredients for hair dye-induced dermatitis and hair loss," J Dermatol Sci 66(1): 12-19.

Shimazu et al. (1964) "Selenoamino Acids: Decrease of Radiation Damage to Amino Acids and Proteins," Science, 143 (3604), 369-371.

Shisler et al. (1998) "Ultraviolet-Induced Cell Death Blocked by a Selenoprotein from a Human Dermatotropic Poxvirus," Science, 279, (5347), 102-105.

Simon et al. (2010) "The Red and the Black," Acc. Chem. Res. 43(11): 1452-1460.

Sing et al. (1985) "Reporting physisorption data for gas/solid systems with special reference to the determination of surface area and porosity," Pure Appl. Chem. 57(4): 603-619.

Smyth et al. (1951) "A study of pigments from red, brown, and buff feathers and hair." Physiol Zool 24, (3), 205-16.

Solano (2014) "Melanins: Skin Pigments and Much More-Types, Structural Models, Biological Functions, and Formation Routes," New J. Sci. 2014, 498276: 1-28.

Solano (publicly available Apr. 2016) "Photoprotection versus photodamage: updating an old but still unsolved controversy about melanin, " Polym. Int. (Nov. 2016) 65(11): 1276-1287.

Song et al. (2007) "Supramolecular Nanofibers by Self-Organization of Bola- amphiphiles through a Combination of Hydrogen Bonding and Π-Π Stacking Interactions," Adv. Mater. 19(3): 416-420.

Søsted et al. (Jul. 2005) "Contact dermatitis to hair dyes in a Danish adult population: an interview-based study," Brit J Dermatol 153(1): 132-135.

Søsted et al. (Jun. 2005) "Allergy to 3-nitro-p-hydroxyethylaminophenol and 4-amino-3-nitrophenol in a hair dye," Contact Dermatitis, 52 (6), 317-9.

Steinmann et al. (2010) "Selenium and sulfur in exchange reactions: a comparative study," J Org Chem 75(19): 6696-6699.

Strube et al. (Mar. 2015) "Site-Specific In Situ Synthesis of Eumelanin Nanoparticles by an Enzymatic Autodeposition-like Process," Biomacromolecules. 16(5): 1608-1613.

Sun et al. (Aug. 2019) "Melanin-dot-mediated delivery of metallacycle for NIR- II/photoacoustic dual-modal imaging-guided chemo-phototherma1 synergistic therapy," Proc Natl Acad Sci USA 116(34): 16729-16735.

Tada et al. (2010) "Scavenging or Quenching Effect of Melanin on Superoxide Anion and Singlet Oxygen," J. Clin. Biochem. Nutr. 46(3): 224-228.

Tadokoro et al. (2003) "UV-induced DNA damage and melanin content in human skin differing in racial/ethnic origin," FASEB J. 17(9): 1177-1179.

Taieb et al. (2011) "Melanins and Melanosomes: Biosynthesis, Biogenesis, Physiological, and Pathological Functions, " Wiley-VCR Verlag Gmbh & Co., Weinheim.

Takkouche et al. (2005) "Personal use of hair dyes and risk of cancer—A meta-analysis," Jama-J Am Med Assoc 293(20): 2516-2525.

Thomson (1974) "The Pigments of Reddish Hair and Feathers," Angew. Chem., Int. Ed. 13(5): 305-312.

Thureau et al. (2012) "Probing the motional behavior of eumelanin and pheomelanin with solid-state NMR spectroscopy: new insights into the pigment properties." Chem.: Eur. J. 18, (34), 10689-700.

Tokura et al. (2018) "Fabrication of Defined Polydopamine Nanostructures by DNA Origami-Templated Polymerization," Angew. Chem. Int. Ed. Engl. 57: 1587- 1591.

Tran et al. (2006) "Chemical and structural disorder in eumelanins: a possible explanation for broadband absorbance," Biophys. J. 90(3): 743-752.

Ursini et al. (1999) "Dual Function of the Selenoprotein PHGPx During Sperm Maturation," Science, 285, (5432), 1393-1396.

Van Neste et al. (2004) "Hair cycle and hair pigmentation: dynamic interactions and changes associated with aging," Micron 35(3): 193-200.

Velasco et al. (2009) "Hair fiber characteristics and methods to evaluate hair physical and mechanical properties," Braz J Pharm Sci 45(1): 153-162.

Vliegenthart et al. (2011) "Compression, crumpling and collapse of spherical shells and capsules," New J. Phys. 13: 045020, pp. 1-24.

Wakamatsu et al. (2003) "The Structure of Neuromelanin as Studied by Chemical Degradative Methods," J. Neurochem. 86(4): 1015-1023.

Walter et al. (2006) "Early use of PbS nanotechnology for an ancient hair dyeing formula," Nano Lett 6(10): 2215-2219.

Wang et al. (Aug. 2018) "Skin Pigmentation-Inspired Polydopamine Sunscreens," Adv. Funct. Mater. 28: 1802127: 1-9.

Wang et al. (Mar. 2020) "Characterization and application of melanin produced by the fast-growing marine bacterium Vibrio natriegens through heterologous biosynthesis." Appl Environ Microbiol DOI: 10.1128/AEM.02749-19.

Wang et al. (publicly available Sep. 2017) "A Novel UV-Shielding and Transparent Polymer Film: When Bioinspired Dopamine-Melanin Hollow Nanoparticles Join Polymers," Acs Appl Mater Inter (Oct. 2017) 9(41): 36281-36289.

Wang et al. (publicly available Sep. 2017) "Tunable, Metal-Loaded Polydopamine Nanoparticles Analyzed by Magnetometry," Chem. Mater. (Oct. 2017) 29(19): 8195-8201.

Watt et al. (2009) "The supramolecular structure of melanin," Soft Matter 5(19): 3754-3760.

Wogelius et al. (2011) "Trace metals as biomarkers for eumelanin pigment in the fossil record," Science 333(6049): 1622-1626.

Wu et al. (2012) "Melanoregulin regulates a shedding mechanism that drives melanosome transfer from melanocytes to keratinocytes," Proc. Natl. Acad. Sci. 109(31): E2101-E2109.

Xia et al. (Oct. 2018) "Selenium-Containing Polymers: Perspectives toward Diverse Applications in Both Adaptive and Biomedical Materials," Macromolecules, 51 (19), 7435-7455.

Xiao et al. (May 2015) "Bio-Inspired Structural Colors Produced via Self- Assembly of Synthetic Melanin Nanoparticles," ACS nano 9(5): 5454-5460.

Xiao et al. (Sep. 2017) "Bioinspired Bright Noniridescent Photonic Melanin Supraballs," Sci. Adv. 3(9): e1701151.

(56) References Cited

OTHER PUBLICATIONS

Xu et al. (2013) "Selenium-Containing Polymers: Promising Biomaterials for Controlled Release and Enzyme Mimics," Acc. Chem. Res. 46 (7), 1647-1658.

Yang et al. (Sep. 2018) "NIR-controlled morphology transformation and pulsatile drug delivery based on multifunctional phototheranostic nanoparticles for photoacoustic imaging-guided photothermal-chemotherapy," Biomaterials 176, 1-12.

Yi et al. (Jul. 2017) "Liquid-immune structural colors with angle-independence inspired from hollow melanosomes," Chem Commun 53(66): 9234-9237.

Young et al. (2017) "Ultraviolet radiation and the skin: Photobiology and sunscreen photoprotection," J Am Acad Dermatol, 76 (3), S100-S109.

Yu et al. (2014) "Formation of polydopamine nanofibers with the aid of folic acid," Angew. Chem. Int. Ed. 53(46): 12600-12604.

Zaidi et al. (2014) "Purification and characterization of melanogenic enzyme tyrosinase from button mushroom" Enzyme Res 120739.

Zaidi et al. (May 2014) "Microbial tyrosinases: promising enzymes for pharmaceutical, food bioprocessing, and environmental industry," Biochem Res Int, 854687.

Zanoni et al. (Feb. 2018) "Allergens of permanent hair dyes induces epidermal damage, skin barrier loss and IL-1 alpha increase in epidermal in vitro model," Food Chem Toxicol 112: 265-272.

Zhang et al. (2012) "Biocompatible Polydopamine Fluorescent Organic Nanoparticles: Facile Preparation and Cell Imaging," Nanoscale 4(18): 5581-5584.

Zhang et al. (publicly available 2016) "$CuSO_4$/$H_2O_2$-Induced Rapid Deposition of Polydopamine Coatings with High Uniformity and Enhanced Stability," Angew Chem Int Ed Engl 55(9): 3054-3057.

Zhou et al. (2014) "Rapidly-Deposited Polydopamine Coating via High Temperature and Vigorous Stirring: Formation, Characterization and Biofunctional Evaluation," Plos One 9(11): e113087, pp. 1-10.

Zhou et al. (Sep. 2019) "Artificial Allomelanin Nanoparticles," ACS Nano 13(10): 10980-10990.

Zhu et al. (Aug. 2018) "A rapid deposition of polydopamine coatings induced by iron (III) chloride/hydrogen peroxide for loose nanofiltration," J Colloid Interf Sci 523: 86-97.

Zucca et al. (2014) "Neuromelanin of the human substantia nigra: an update," Neurotox. Res. 25: 13-23.

\* cited by examiner

FIG. 1A
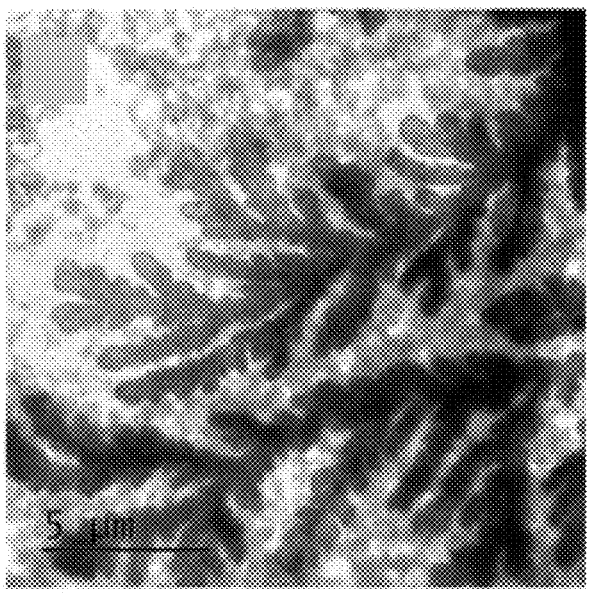
FIG. 1B
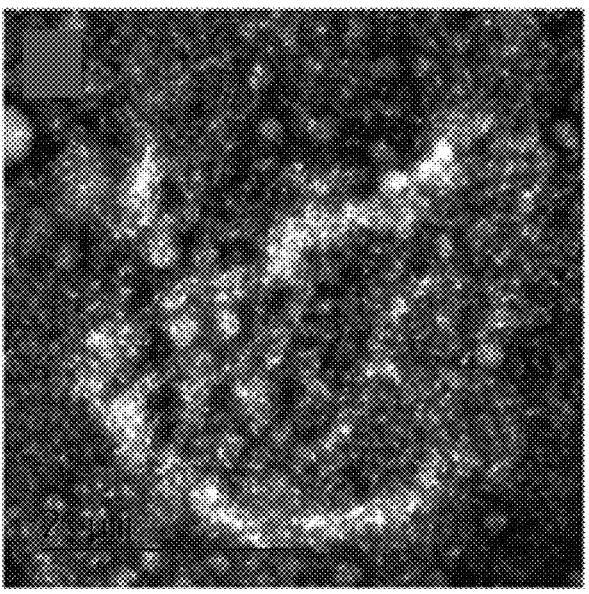
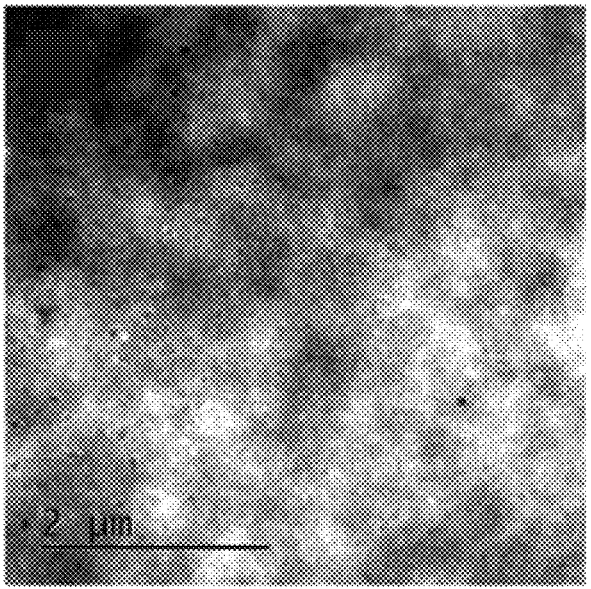
FIG. 1C
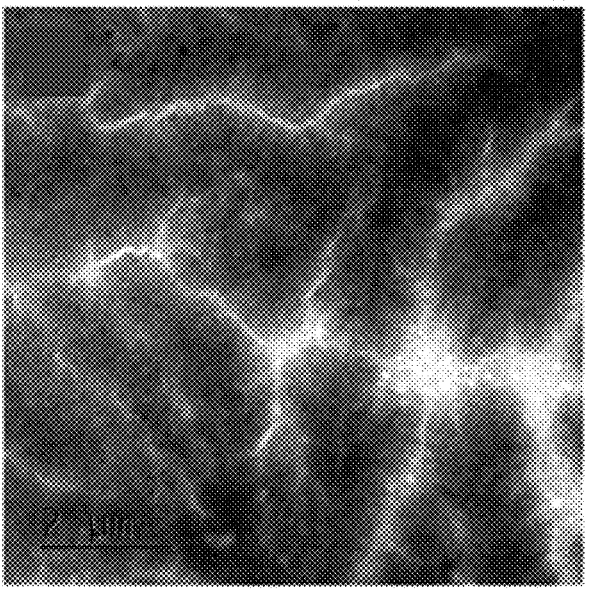
FIG. 1D

MELANIN HAIR DYE WITH THICKENERS

CROSS-REFERENCE TO RELATED APPLICATIONS

This application claims the benefit of priority to U.S. Provisional Patent Application No. 63/353,891, filed Jun. 21, 2022, which is hereby incorporated by reference in its entirety.

STATEMENT REGARDING FEDERALLY SPONSORED RESEARCH OR DEVELOPMENT

This invention was made with government support under Award Number FA9550-18-1-0142 awarded by the Air Force Office of Scientific Research. The government has certain rights in the invention.

BACKGROUND OF INVENTION

From countering the effects of aging or illness to expressing one's uniqueness, people have dyed their hair for a myriad of reasons throughout the ages. There are various conventional methods and agents for dying hair, some of which are permanent dyes and others are semi-permanent, for example. Due to such widespread use, hair dye industries are now among the most profitable in the cosmetics sector. Some studies suggest that over 50% of the population in developed countries has dyed their hair at least once in their life. However, conventional methods suffer from requiring long application times, harsh, potentially carcinogenic, reagents, poor persistence, allergic reactions to reagents, and/or poor coloration.

New approaches to hair dying include use of nanoparticles, for example. While the synthesis of gold nanoparticles in human hair has been proposed as an effective way to darken white hair, the long reaction time required by this protocol (e.g., 16 days) hampers its application as an effective hair dyeing method. A much faster approach involves the use of graphene-based sheets for coloration. Hair coated with this material showed good antistatic performance and heat dissipation properties, however, the method was expensive and only produced a single color—black.

Human hair is comprised mainly of protein, at 65-95% by weight. Keratin, the most abundant component, is a group of insoluble protein complexes which impart elasticity, suppleness and resistance to the fibers. Melanin, nature's hair pigment, is mainly distributed in the middle layer of the hair shaft or cortex and is embedded between keratin fibers, where it makes up only 1 to 3% of human hair by weight. These nanometer-scale granular pigments (200-800 nm) generate the naturally beautiful colors found in human hair. Colors arise from the distribution, concentration, and blending of two types of melanin: brown and black eumelanins, and less commonly, red pheomelanins. It follows then that the reduction or disappearance of melanin from hair fibers is the phenomenon that leads to color loss and consequent hair greying and eventually whitening.

Thus, a very interesting approach to darken hair and a desirable alternative to current formulations would be a synthetic version of the naturally occurring nano-sized melanin pigment particles to reestablish color of the hair fibers. However, recent successful human hair dyeing using synthetic melanin required high concentrations of potentially toxic heavy metals such as copper and iron as chelators. Moreover, these demonstrations were limited to a dark brown coloration and lack extensive imaging and characterization of the dyeing mechanism. In other demonstrations of using synthetic melanins, strong oxidative conditions using sodium periodate were employed for successful dopamine deposition on human hair, but this method may not be suitable for widespread use in an at-home or salon application.

It is thus apparent that there is need in the art for new methods and materials for dying hair, which are effective but also address the above challenges associated with conventional approaches, for example by being mild, tunable, biocompatible, metal-free, long-lasting, and further being easy to apply to hair.

SUMMARY OF THE INVENTION

Included herein are methods and materials for nontoxic, biocompatible, optionally metal-free, tunable, and long-lasting coloration of human hair. More particularly, provided herein are methods, and associated formulations, for efficient formation and deposition of synthetic melanin to human hair, thereby coloration of hair, whereby the hair treatment formulation is viscous enough for treatment of hair without substantially loss of the formulation with further allows an easier application process that includes exposing the hair to the treatment formulation for an extended amount of time. For example, the hair treatment formulation, or viscous solution, can be applied and left on the hair, such as if it were a cream or gel, without requiring soaking the hair in a bath. Different colors can be achieved by tuning reaction conditions such as temperature and solution phase composition. These methods, and associated materials, can be used in salons and at home, for example, without degradation of the resulting colored hair and safety of the user of the present materials and methods.

Aspects disclosed herein include a method of treating hair of a subject with one or more artificial melanin materials, the method comprising: contacting, in a viscous solution, one or more artificial melanin precursors with an oxidizing agent in the presence of a solution-thickening agent and the hair of said subject to form said one or more artificial melanin material; wherein said one or more artificial melanin materials associates with said hair of said subject, thereby treating the hair of said subject. In an embodiment, polymerization of the melanin precursors happens when preparing the solution, for example, upon addition of the oxidizing agent, and the solution is quickly applied it to the hair before all the melanin monomers have undergone complete polymerization. In an embodiment, the hair is contacted with the solution comprising melanin precursors and oxidizing agent for at least a portion of the duration of the polymerization process, for example, to allow effective association with and/incorporation into the hair. In an embodiment, the solution is added to the hair immediately after adding the oxidizing agent (e.g., a base) base, for example, at a time at which the polymerization starts to occur or is proximate in time with initiation of polymerization, so the melanin material is forming when it is in contact with the hair. The methods herein also include processes wherein the melanin materials are contacted with the hair after a substantial extent, or substantially all, of the polymerization reaction has already occurred.

Aspects disclosed herein include a method of treating hair of a subject with one or more artificial melanin materials, the method comprising: contacting, in a viscous solution, one or more artificial melanin precursors and/or one or more artificial melanin materials with an oxidizing agent in the presence of a solution-thickening agent and the hair of said subject to form one or more other artificial melanin materials; wherein said one or more other artificial melanin materials associate with said hair of said subject, thereby treating the hair of said subject.

Aspects disclosed herein include a viscous solution for hair treatment, the viscous solution comprises: one or more artificial melanin precursors; and one or more solution-thickening agents.

Aspects disclosed herein include a viscous solution for hair treatment, the viscous solution comprises: one or more artificial melanin precursors and/or one or more artificial melanin materials; and one or more solution-thickening agents.

Aspects disclosed include thickening agents that are capable of forming a hydrogel, such as hyaluronic acid once it gels or cross-links.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIGS. 1A-1D: 5 mg/mL of dopamine polymerized in 5 mg/mL of thickeners. FIG. 1A: Hyaluronic acid. FIG. 1B: Hydroxyethylcellulose. FIG. 1C: *Sclerotium* Gum. FIG. 1D: Xanthan Gum.

STATEMENTS REGARDING CHEMICAL COMPOUNDS AND NOMENCLATURE

Figure 2:
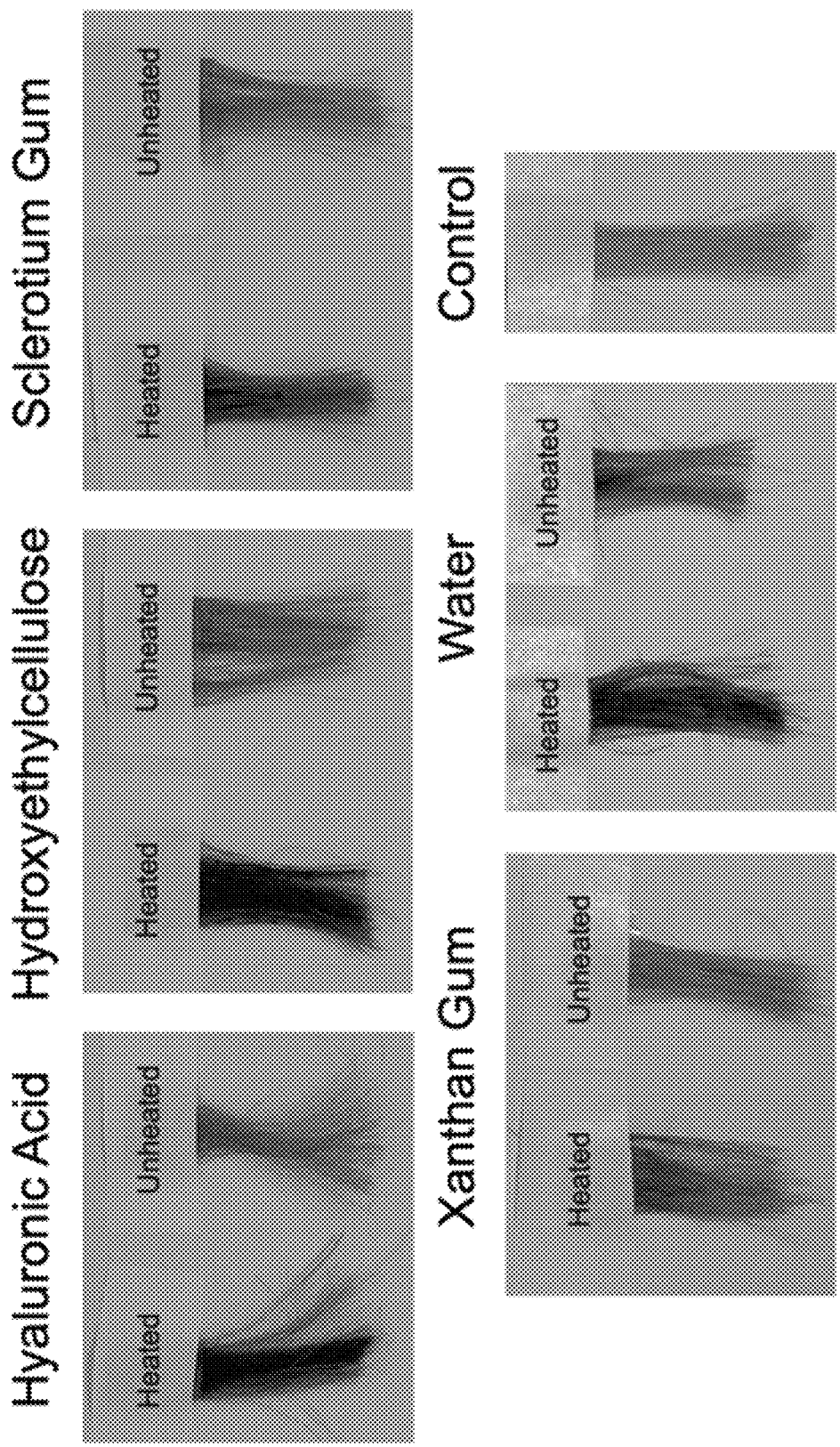
FIG. 2: 5 mg/mL of dopamine polymerized in water or 5 mg/mL of the following thickeners and 3% $NH_4OH$: hyaluronic acid, hydroxyethylcellulose, *Sclerotium* gum, xanthan gum. The solution was either unheated or heated to 40° C. The polymerization was left to go for two hours before the hair was washed with water and shampoo.

In general, the terms and phrases used herein have their art-recognized meaning, which can be found by reference to standard texts, journal references and contexts known to those skilled in the art. The following definitions are provided to clarify their specific use in the context of the invention.

The term "amine compound" refers to a compound or molecule having one or more amine groups, where each amine group may be a primary, secondary, or tertiary amine group.

Wherein the term "alpha carbon" is used to describe an amine compound, the alpha carbon refers to a carbon closest to an N of an amine group. An alpha carbon that is a secondary carbon has one H directly bound to it (e.g., a secondary alpha carbon is bound to an N, two other carbons, and one H). An alpha carbon that is a tertiary carbon has no H directly bound to it (e.g., a tertiary alpha carbon is bound to an N and three other carbons).

The term "melanin" generally refers to one or more compounds or materials that function as a pigment, such as when internalized or taken up by a biological cell, for example. It is also noted that melanin is not necessarily taken up by cells. Melanin can be used for forming cell walls in fungi, for example, such as to provide rigidity, defense mechanisms, and more. In another illustrative example, melanin is used by birds, such as where melanin is organized in a matrix of keratin or similar type of biological material, where it can be organized into monolayers or multilayers to provide structural color, warmth, and more. A melanin compound or material may be, but is not limited to, a melanin monomer, a melanin oligomer, a melanin polymer, a melanin nanoparticle, a melanin layer (e.g., a melanin thin film or coating), or other melanin material, for example. For example, melanin nanoparticles internalized by a biological cell function as a pigment in the cell.

The terms "artificial melanin" and "synthetic melanin" are used interchangeably herein and refer to one or more melanin compounds, molecules, or materials, such as melanin monomers, melanin oligomers, or melanin nanoparticles, that are synthesized and are at least partially, or preferably entirely, not derived from or not extracted from a natural source, such as a biological source, a living organism, or a once living organism. The terms "synthetic" and "artificial" are used interchangeably herein when referring to a melanin or a material comprising a melanin. The terms "synthetic melanin nanoparticles" and "artificial melanin nanoparticles" are used interchangeably herein, and are intended to have the same meaning throughout the present disclosure, and refer to nanoparticles formed of artificial melanin, such as artificial melanin monomers and/or artificial melanin oligomers. The terms "synthetic melanin thin film" and "artificial melanin thin film" are used interchangeably herein, and are intended to have the same meaning throughout the present disclosure, and refer to a thin film formed of artificial melanin, such as artificial melanin monomers and/or artificial melanin oligomers. The terms "synthetic melanin layer" and "artificial melanin layer" are used interchangeably herein, and are intended to have the same meaning throughout the present disclosure, and refer to a layer formed of artificial melanin, such as artificial melanin monomers and/or artificial melanin oligomers. An artificial melanin nanoparticle, artificial melanin thin film, artificial melanin layer, and any compound, material, or formulation comprising any of these, comprises artificial melanin monomers, artificial melanin oligomers, and/or artificial melanin polymers. Optionally, an artificial melanin nanoparticle, artificial melanin thin film, artificial melanin layer, and any compound, material, or formulation comprising any of these, consists of or consists essentially of artificial melanin, such as artificial melanin monomers, artificial melanin oligomers, and/or artificial melanin polymers. Optionally, an artificial melanin nanoparticle, artificial melanin thin film, artificial melanin layer, and any compound, material, or formulation comprising any of these, is free (or substantially free) of artificial melanin monomers and comprises artificial melanin oligomers and/or artificial melanin polymers. Optionally, such as optionally in any of Aspects 1-47, each artificial melanin monomer, artificial melanin oligomer, and artificial melanin polymer of an artificial melanin nanoparticle, artificial melanin thin film, artificial melanin layer, and any compound, material, or formulation comprising any of these, is not bound to, conjugated to, attached to, coated by, encompassed by or chemically otherwise associated with a natural or biological proteinaceous lipid. A natural or biological proteinaceous lipid refers to a naturally or biologically derived lipid or a lipid extracted from a natural or biological source, such as a once living organism, said lipid comprising one or more proteins such as the lipid (plasma) membrane of a melanocyte or melanosome). Optionally, each artificial melanin monomer, artificial melanin oligomer, and artificial melanin polymer of an artificial melanin nanoparticle, artificial melanin thin film, artificial melanin layer, and any compound, material, or formulation comprising any of these, is not bound to, conjugated to, attached to, coated by, encompassed by or otherwise chemically associated with a natural or biological lipid (e.g. a lipid bilayer, lipid membrane or phospholipid compound). A natural or biological lipid refers to a naturally or biologically derived lipid or a lipid extracted from a natural or biological source, such as a once living organism. Optionally, any artificial melanin monomer, artificial melanin oligomer, and artificial melanin polymer of an artificial melanin nanoparticle, artificial melanin thin film, artificial melanin layer, and any compound, material, or formulation comprising any of these, is bound to, conjugated to, attached to, coated by, encompassed by, and/or otherwise associated with a synthetic or artificial lipid or with a synthetic or artificial phospholipid. A synthetic or artificial lipid refers to a synthesized lipid that is not derived from or is not extracted from a natural or biological source, such as a once living organism.

The term "artificial melanin precursor" refers to a compound or material that can form an artificial melanin material after a chemical reaction, such as after a chemical reaction with an oxidation agent. An artificial melanin precursor can be, but is not necessarily, itself a melanin. For example, an artificial melanin precursor can be, but is not necessarily, a melanin monomer. For example, contacting artificial melanin precursors such as melanin monomers with an oxidizing agent can result in oxidative oligomerization (or, polymerization) among the artificial melanin precursors thereby forming artificial melanin material(s).

The term "selenomelanin" refers to melanin comprising selenium. For example, a selenomelanin material comprises selenium. Optionally, such as optionally in any of Aspects 1-47, a chemical formula of a selenomelanin material comprises selenium (e.g., at least one selenium atom).

In certain embodiments, the term "pheomelanin" refers to a melanin whose chemical formula comprises at least one substituted or unsubstituted benzothiazine, at least one substituted or unsubstituted benzothiazole, at least one substituted or unsubstituted benzoselenazole, at least one substituted or unsubstituted benzoselenazine, at least one derivative of any of these, or any combination of these. In certain embodiments, the term pheomelanin refers to a melanin made from L-DOPA and cysteine, whose chemical formula comprises at least one substituted or unsubstituted benzothiazine, at least one substituted or unsubstituted benzothiazole, at least one substituted or unsubstituted benzoselenazole, at least one substituted or unsubstituted benzoselenazine, at least one derivative of any of these, or any combination of these. In certain embodiments, a selenium pheomelanin refers to a melanin whose chemical formula comprises at least one substituted or unsubstituted benzoselenazole, at least one substituted or unsubstituted benzoselenazine, at least one derivative of any of these, or any combination of these.

In certain embodiments, the term eumelanin refers to a melanin whose chemical formula comprises at least one dihydoxyindole (DHI) (e.g., 5,6-dihydroxyindole), at least one dihydroxyindole-2-carboxylic acid (DHICA) (e.g., 5,6-dihydroxyindole-2-carboxylic acid), or a combination of these.

As used herein, treatment of hair and treating hair refer to changing a color of hair, such as, but not necessarily, making hair darker, such as, but not necessarily, more brown or more black, and/or increasing persistence of a hair color, such as, but not necessarily, increasing the persistence of a dark color (e.g., brown or black) of hair that is initially the dark color. Any of the methods of treating hair and any of the artificial melanin materials disclosed herein can be used for treating hair. A change in a hair color as a result of treating hair Optionally, such as optionally in any of Aspects 1-47, but not necessarily, corresponds to a darkening of the hair color. A change in a hair color as a result of treating hair Optionally, such as optionally in any of Aspects 1-47, but not necessarily, corresponds to the hair color becoming more brown or more dark. Optionally, such as optionally in any of Aspects 1-47, but not necessarily, a change in a hair color as a result of treating hair corresponds to any change in color of the hair. Exemplary changes in hair color as a result of treating hair, such as according to embodiments disclosed herein, include, but are not limited to, hair becoming: a dark brown color, a brown color with shades of red, an orange or dark orange color, a brown color, a brown color with orange shades, and/or a bright blond color.

The term "persistence" of a hair colors refers to limited, low, or lack of change in the hair color, such as in response to time and/or exposure to one or more conditions or processes that can otherwise affect hair color, such as rinsing and/or washing of the hair with a solvent (e.g., water) and/or a surfactant (e.g., shampoo). A hair color or a change in hair color characterized as persistent refers to the hair color or the change in hair color having persistence. A persistent change in hair color refers to the hair color resulting from the treating of the hair (e.g., the color obtained after treating hair) having persistence. Hair color persistence can be characterized by absolute and/or relative change, if any, of RGB color intensities and/or RGB color ratios corresponding to the hair color.

The term "aging", when used in reference to artificial melanin nanoparticles herein, refers to a process by which synthesized and isolated artificial melanin nanoparticles oxidize, and optionally further darker, over time during exposure to oxygen, such due to exposure to air. Isolated artificial melanin nanoparticles can be artificial melanin nanoparticles that are purified, such as by centrifugation, and re-dispersed in water, such as ultrapure water, or optionally another solvent or solvent solution. For example, artificial melanin nanoparticles may age if the particles are dispersed in water and are stored in a vial with the vial's top on (closed) and with the top not being opened for some extended period of time, because there is residual oxygen in the container. The aging process can alter certain properties or characteristics of artificial melanin nanoparticles, such as increasing solubility in organic solvent or decreasing toxicity to certain living biological cells. For example, without wishing to be bound by any particular theory, in some embodiments, freshly synthesized artificial melanin nanoparticles can be dynamic and shed monomers or oligomers into a cell when internalized by the cell. For example, without wishing to be bound by any particular theory, in some embodiments, freshly synthesized artificial melanin nanoparticles can be dynamic and have surface chemistry oxidation state that is not optimal for living cells when internalized by cells. For example, without wishing to be bound by any particular theory, in some embodiments, the aging process can lead to more crosslinking or otherwise chemical association between melanin compounds (monomers, oligomers) in the artificial melanin nanoparticles, potentially leading to reduced cytotoxicity, such as due to reduced shedding of melanin compounds into the cell and/or altering or stabilizing of the particles' surface chemistry.

The term "nanoparticle" as used herein, refers to a physical particle having at least one size characteristic or physical dimension less than less than 1 µm. Optionally, such as optionally in any of Aspects 1-47, term "nanoparticle" as used herein, refers to a physical particle whose longest size characteristic or physical dimension is less than 1 µm.

The term "size characteristic" refers to a property, or set of properties, of a particle that directly or indirectly relates to a size attribute. According to some embodiments, a size characteristic corresponds to an empirically-derived size characteristic of a particle(s) being detected, such as a size characteristic based on, determined by, or corresponding to data from any technique or instrument that may be used to determine a particle size, such as electron microscope (e.g., SEM and TEM) or a light scattering technique (e.g., DLS). For example, a size characteristic can correspond to a spherical particle exhibiting similar or substantially same properties, such as aerodynamic, hydrodynamic, optical, and/or electrical properties, as the particle(s) being detected). According to some embodiments, a size characteristic corresponds to a physical dimension, such as a cross-sectional size (e.g., length, width, thickness, or diameter).

The term "particles" refers to small solid objects that may be dispersed and/or suspended in a fluid (e.g., liquid). For example, a slurry, a dispersion, and a suspension each include particles in a fluid. The terms "particle" and "particulate" may be used interchangeably. An exemplary particle is an artificial melanin nanoparticle. A plurality of particles may be associated together to form an agglomerate of particles. Generally, the term "particle", such as "nanoparticle" or "melanin nanoparticle", refers to an individual particle rather than to an agglomerate of such individual particles.

The term "dispersed" refers to species, such as particles, in a fluid forming a dispersion. As used herein, the term "dispersion" broadly refers to a mixture of one or more chemical species, such as particles, in a fluid, such as the art-recognized meaning of solution, dispersion, and/or suspension. The chemical species, such as particles, dispersed in a dispersion can be referred as a dispersed species. Optionally, such as optionally in any of Aspects 1-47, a dispersion is a mixture of particles, such as artificial melanin particles, in a liquid, such as a solvent. Optionally, such as optionally in any of Aspects 1-47, but not necessarily, a dispersion is a homogeneous mixture. In the context of a dispersion, the term "homogeneous" refers to a liquid mixture that appears uniform to the naked eye. In contrast, a heterogenous liquid mixture includes particles that are precipitated from or suspended in the liquid mixture and are large enough to be distinctly identifiable by the naked eye in the liquid mixture. A heterogeneous liquid mixture includes, for example, sedimented and/or sedimenting particles. Optionally, such as optionally in any of Aspects 1-47, but not necessarily, the term "dispersion" is broadly intended to include solutions and dispersions, such as colloids, which are not heterogenous liquid mixtures. Optionally, such as optionally in any of Aspects 1-47, but not necessarily, a dispersion is a microscopically homogenous, or uniform, mixture of particles in a liquid, such as a solvent. Optionally, such as optionally in any of Aspects 1-47, but not necessarily, a dispersion is thermodynamically favored remain stably dispersed or is thermodynamically favored to segregate by sedimentation but wherein sedimentation is kinetically slowed or prevented. Particles, of a dispersion, that are characterized as stably dispersed remain dispersed in the dispersion and do not sediment or precipitate out of the liquid, of the dispersion, for at least 5 hours, preferably at least 12 hours, preferably at least 24 hours, and more preferably at least 1 week, under normal temperature and pressure (NTP) and exposure to air. In embodiments, particles that are not or cannot be dispersed in a fluid refer to particles that form precipitates or sediments upon being mixed in the fluid.

The term "size stable" refers to stability of particles in a dispersion with respect to a size characteristic of said particles. Optionally, such as optionally in any of Aspects 1-47, particles in a dispersion characterized as size stable are characterized by a size characteristic being within 50%, within 40%, within 30%, preferably within 20%, more preferably within 15%, still more preferably within 10%, further more preferably within 5%, or equivalent to a reference or initial size characteristic, under given conditions and optionally for a given time. For example, nanoparticles of a dispersion characterized as size-stable in the dispersion having a pH of at least 11, with respect to an average size of the nanoparticle in the dispersion having a pH of 7, have an average size in the pH 11 dispersion that is within 50%, within 40%, within 30%, preferably within 20%, more preferably within 15%, still more preferably within 10%, further more preferably within 5%, or equivalent to an average size of the otherwise equivalent nanoparticles in the otherwise equivalent dispersion having a pH of 7. Optionally, such as optionally in any of Aspects 1-47, but not necessarily, nanoparticles characterized as size stable as so size stable for time that is at least 1 hour to 5 hours, preferably at least hours to 12 hours, more preferably at least 12 hours to 1 week, still more preferably at least 1 week.

The term "strong oxidizing agent" refers to a substance (e.g., compound, molecule, material) having a greater ability for subtracting, removing, or accepting one or more electron from another other substance compared to oxygen gas, including oxygen gas dissolved in a solution. The greater ability may be due to thermodynamic, kinetic, and/or electrochemical characteristics thereof. Optionally, a strong oxidizing agent has a greater or more positive standard electrode potential than 02.

The term "U" in a unit of concentration, such as "U/mL", refers to "unit of activity" and is a known term of art referring to enzyme catalytic activity. A unit "U" refers to the amount of enzyme that catalyzes the conversion of 1 micromole (µmole) of a substrate per minute. Thus, 1 enzyme unit (U)=1 µmol/min, where µmol refers to the amount of substrate converted. Because each enzyme has a unique substrate, a unit of activity is different for one enzyme versus another.

The term "structural color" refers to the generation of color due to interference of visible light structural features, such as a film or layer or a microstructured surface. A layer of melanin nanoparticles may exhibit color due to interference of visible light with the microstructure of the layer, rather than solely due to pigmentation. Without wishing to be bound by any particular theory, the effect of structural color can enable a spectrum on non-fading, non-photobleaching colors which can be iridescent or non-iridescent. Without wishing to be bound by any particular theory, high refractive index of melanin and synthetic melanin, and its broadband absorption across the visible spectrum allows it to interact with light in such a way that a multitude of colors are produced.

The term "peak size" size refers to the statistical mode, or peak frequency, of a particle size distribution, or the particle size most commonly found in the particle size distribution. A particle size distribution can be measured using dynamic light scattering, for example.

The term "sphere" as used herein, in the usual and customary sense, refers to a round or substantially round geometrical object in three-dimensional space that is substantially the surface of a completely round ball, analogous to a circular object in two dimensions. A sphere may be defined mathematically as the set of points that are all at the same or substantially all at the same distance r from a given point, but in three-dimensional space, where r is the radius of the mathematical ball and the given point is the center or substantially the center of the mathematical ball. In embodiments, the longest straight line through the ball, connecting two points of the sphere, passes through the center and its length is thus twice the radius; it is a diameter of the ball. A nanosphere is a nanoparticle having a radius of less than 1 µm.

The terms "ultraviolet induced damage" and "UV induced damage" as used interchangeably herein refer, in the usual and customary sense, to chemical changes attending irradiation of light of sufficient energy. UV induced damage can include scission of nucleic acids (e.g., DNA or RNA), and breaking of bonds in proteins, lipids, and other physiological molecules. For example, the damage can be damage resulting from reactive oxygen species (ROS).

The terms "reactive oxygen species" and "ROS" as used interchangeably herein refer, in the usual and customary sense, to transient species, typically formed during exposure to radiation (e.g., UV irradiation) capable of inducing oxidative decomposition.

The terms "cell" and "biological cell" are used interchangeably are refer to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., *Spodoptera*) and human cells. A "viable cell" is a living biological cell.

The term "self-assembly" refers to a process in which individual elements assemble into a network or organized structure without external direction. In an embodiment, self-assembly leads to a decrease in entropy of a system. In an embodiment, self-assembly may be induced, or initiated, via contacting or reacting the individual elements, optionally at a certain critical concentration, and/or via temperature and/or via pressure. A "self-assembled structure" is a structure or network formed by self-assembly. In an embodiment, self-assembly is a polymer crystallization process. The Gibbs free energy of the self-assembled structure is lower than of the sum of the individual components in their non-organized arrangement prior to self-assembly under otherwise identical conditions (e.g., temperature and pressure). In an embodiment, entropy of a self-assembled structure is lower than that of the sum of the individual components in their non-organized arrangement prior to self-assembly under otherwise identical conditions (e.g., temperature and pressure). For example, artificial melanin nanoparticles of this disclosure can form by self-assembly of a plurality of oligomers and/or melanin monomers. For example, structures or layers (e.g., films) for artificial melanin nanoparticles may form by self-assembly, such as structures or layers formed of artificial melanin nanoparticles and exhibiting structural color.

The term "substantially" refers to a property, condition, or value that is within 20%, 10%, within 5%, within 1%, optionally within 0.1%, or is equivalent to a reference property, condition, or value. The term "substantially equal", "substantially equivalent", or "substantially unchanged", when used in conjunction with a reference value describing a property or condition, refers to a value that is within 20%, within 10%, optionally within 5%, optionally within 1%, optionally within 0.1%, or optionally is equivalent to the provided reference value. For example, a diameter is substantially equal to 100 nm (or, "is substantially 100 nm") if the value of the diameter is within 20%, optionally within 10%, optionally within 5%, optionally within 1%, within 0.1%, or optionally equal to 100 nm. The term "substantially greater", when used in conjunction with a reference value describing a property or condition, refers to a value that is at least 1%, optionally at least 5%, optionally at least 10%, or optionally at least 20% greater than the provided reference value. The term "substantially less", when used in conjunction with a reference value describing a property or condition, refers to a value that is at least 1%, optionally at least 5%, optionally at least 10%, or optionally at least 20% less than the provided reference value.

The terms "keratinocyte" and "keratinocytes" as used herein, refer to the predominant cell type in the epidermis, the outermost layer of the skin, constituting the majority (e.g., 90%-95%) of the cells found there. Keratinocytes are found in the deepest basal layer of the stratified epithelium that comprises the epidermis, and are sometimes referred to as basal cells or basal keratinocytes. Keratinocytes are maintained at various stages of differentiation in the epidermis and are responsible for forming tight junctions with the nerves of the skin. They also keep Langerhans cells of the epidermis and lymphocytes of the dermis in place. Keratinocytes contribute to protecting the body from UV radiation by taking up melanosomes. Keratinocytes contribute to protecting the body from UV radiation by taking up melanosomes, vesicles containing the endogenous photoprotectant melanin, from epidermal melanocytes. Each melanocyte in the epidermis has several dendrites that stretch out to connect it with many keratinocytes. The melanin is then stored within keratinocytes and melanocytes in the perinuclear area as "supranuclear caps", where it protects the DNA from UV-induced damage. In addition to their structural role, keratinocytes play a role in immune system function. The skin is the first line of defense and keratinocytes serve as a barrier between an organism and its environment. In addition to preventing toxins and pathogens from entering an organisms body, they prevent the loss of moisture, heat and other important constituents of the body. In addition to their physical role, keratinocytes serve a chemical immune role as immunomodulaters, responsible for secreting inhibitory cytokines in the absence of injury and stimulating inflammation and activating Langerhans cells in response to injury. Langerhans cells serve as antigen-presenting cells when there is a skin infection and are the first cells to process microbial antigens entering the body from a skin breach.

The terms "under conditions suitable to afford uptake", "taken up" and "take up" as used herein, refer, in the usual and customary sense, to experimental conditions well known in the art which allow uptake (e.g., endocytosis) of a species into a cell. In some embodiments, the term "internalized" when referring to particles internalized in or by a biological cell, refers to particles taken up by the biological cell, such as by, but not limited to, formation of perinuclear caps.

The term "endocytosis" as used herein, refers to a form of active transport in which a cell transports molecules (such as proteins) into the cell by engulfing them in an energy-using process. Endocytosis includes pinocytosis and phagocytosis. Pinocytosis is a mode of endocytosis in which small particles are brought into the cell, forming an invagination, and then suspended within small vesicles. These pinocytotic vesicles subsequently fuse with lysosomes to hydrolyze (break down) the particles. Phagocytosis is the process by which a cell engulfs a solid particle to form an internal compartment known as a phagosome.

The terms "treating" or "treatment" as used herein, refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating," and conjugations thereof, include prevention of an injury, pathology, condition, or disease.

The term "effective amount" as used herein, refers to an amount sufficient to accomplish a stated purpose (e.g. Achieve the effect for which it is administered, treat a disease, reduce one or more symptoms of a disease or condition, and the like). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

The term "administering" as used herein, refers to oral administration, administration as an inhaled aerosol or as an inhaled dry powder, suppository, topical contact, intravenous, parenteral, intraperitoneal, intramuscular, intralcsional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compound of the invention can be administered alone or can be co-administered to the patient. Co-administration is meant to include simultaneous or sequential administration of the compound individually or in combination (more than one compound or agent). The compositions of the present invention can be delivered transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, J Biomater Sci. Polym. Ed. 7:623-645, 1995; as biodegradable and injectable gel formulations (see, e.g., Gao Pharm. Res. 12:857-863, 1995); or, as microspheres for oral administration (see, e.g., Eyles, J Pharm. Pharmacol. 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, J. Microencapsul. 13:293306, 1996; Chonn, Curr. Opin. Biotechnol. 6:698-708, 1995; Qstio, Am. J Hasp. Pharm. 46: 1576-1587, 1989).

The term "contacting" may include allowing two species to react, interact, or physically touch, wherein the two species may be, for example, a pharmaceutical composition as provided herein and a cell. In embodiments contacting includes, for example, allowing a pharmaceutical composition as described herein to interact with a cell or a patient.

The terms "analog" and "analogue" are used interchangeably and are used in accordance with their plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound, including isomers thereof. Accordingly, an analog is a compound that is similar or comparable in function and appearance but not in structure or origin to a reference compound.

Except where otherwise specified, the term "molecular weight" refers to an average molecular weight. Except where otherwise specified, the term "average molecular weight," refers to number-average molecular weight. Number average molecular weight is defined as the total weight of a sample volume divided by the number of molecules within the sample. As is customary and well known in the art, peak average molecular weight and weight average molecular weight may also be used to characterize the molecular weight of the distribution of polymers within a sample.

The term "weight-average molecular weight" ($M_w$) refers to the average molecular weight defined as the sum of the products of the molecular weight of each polymer molecule ($M_i$) multiplied by its weight fraction ($w_i$): $M_w = \Sigma w_i M_i$. As is customary and well known in the art, peak average molecular weight and number average molecular weight may also be used to characterize the molecular weight of the distribution of polymers within a sample.

The term "wt. %" or "wt %" refers to a weight percent, or a mass fraction represented as a percentage by mass. The term "at. %" or "at %" refers to an atomic percent, or an atomic ratio represented as a percentage of a type of atom with respect to total atoms in a given matter, such as a molecule, compound, material, nanoparticle, polymer, dispersion, etc.

The term "oligomerization" refers to a chemical process of converting a monomer or a mixture of monomers into an oligomer. The term "oxidative oligomerization" refers to a chemical process of oligomerization that includes chemical oxidation of one or more monomers to form an oligomer. An oligomerization is a polymerization process, wherein an oligomer is formed as a result of the polymerization.

As used herein, the term "polymer" refers to a molecule composed of repeating structural units connected by covalent chemical bonds often characterized by a number of repeating units, also referred to as base units (e.g., greater than or equal to 2 base units). As used herein, a term "polymer" is inclusive of an "oligomer" (i.e., an oligomer is a polymer; i.e., a polymer is optionally an oligomer). An "oligomer" refers to a molecule composed of repeating structural units, also referred to as base units, connected by covalent chemical bonds often characterized by a number of repeating units less such that the oligomer is a low molecular weight polymer. Optionally, such as optionally in any of Aspects 1-47, but not necessarily, for example, an oligomer has equal to or less than 100 repeating units. Optionally, such as optionally in any of Aspects 1-47, but not necessarily, for example, an oligomer has a lower molecular weight less than or equal to 10,000 Da. Oligomers may be the polymerization product of one or more monomer precursors. Polymerization of one or more monomers, or monomer precursors, resulting in formation of an oligomer may be referred to as oligomerization. An oligomer optionally includes 100 or less, 50 or less, 15 or less, 12 or less, 10 or less, or 5 or less repeating units (or, "base units"). An oligomer may be characterized has having a molecular weight of 10,000 Da or less, 5,000 Da or less, 1,000 Da or less, 500 Da or less, or 200 Da or less. A dimer, a trimer, a tetramer, or a pentamer is an oligomer having two, three, four, or five, respectively, repeating units, or base units. Polymers can have, for example, greater than 100 repeating units. Polymers can have, for example, a high molecular weight, such as greater than 10,000 Da, in some embodiments greater than or equal to 50,000 Da or greater than or equal to 100,000 Da. The term polymer includes homopolymers, or polymers consisting essentially of a single repeating monomer subunit. The term polymer also includes copolymers which are formed when two or more different types of monomers are linked in the same polymer. Copolymers may comprise two or more monomer subunits, and include random, block, brush, brush block, alternating, segmented, grafted, tapered and other architectures. Useful polymers include organic polymers or inorganic polymers that may be in amorphous, semi-amorphous, crystalline or semi-crystalline states. Polymer side chains capable of cross linking polymers (e.g., physical cross linking) may be useful for some applications.

An "oligomer" refers to a molecule composed of repeating structural units, also referred to as base units, connected by covalent chemical bonds often characterized by a number of repeating units less than that of a polymer (e.g., equal to or less than 100 repeating units) and a lower molecular weights (e.g. less than or equal to 10,000 Da) than polymers. Oligomers may be the polymerization product of one or more monomer precursors. Polymerization of one or more monomers, or monomer precursors, resulting in formation of an oligomer may be referred to as oligomerization. An oligomer optionally includes 100 or less, 50 or less, 15 or less, 12 or less, 10 or less, or 5 or less repeating units (or, "base units"). An oligomer may be characterized has having a molecular weight of 10,000 Da or less, 5,000 Da or less, 1,000 Da or less, 500 Da or less, or 200 Da or less. A dimer, a trimer, a tetramer, or a pentamer is an oligomer having two, three, four, or five, respectively, repeating units, or base units.

As used herein, the term "group" may refer to a functional group of a chemical compound. Groups of the present compounds refer to an atom or a collection of atoms that are a part of the compound. Groups of the present invention may be attached to other atoms of the compound via one or more covalent bonds. Groups may also be characterized with respect to their valence state. The present invention includes groups characterized as monovalent, divalent, trivalent, etc. valence states.

The term "moiety" refers to a group, such as a functional group, of a chemical compound or molecule. A moiety is a collection of atoms that are part of the chemical compound or molecule. The present invention includes moieties characterized as monovalent, divalent, trivalent, etc. valence states. Generally, but not necessarily, a moiety comprises more than one functional group.

As used herein, the term "substituted" refers to a compound wherein one or more hydrogens is replaced by another functional group, provided that the designated atom's normal valence is not exceeded. An exemplary substituent includes, but is not limited to: a halogen or halide, an alkyl, a cycloalkyl, an aryl, a heteroaryl, an acyl, an alkoxy, an alkenyl, an alkynyl, an alkylaryl, an arylene, a heteroarylene, an alkenylene, a cycloalkenylene, an alkynylene, a hydroxyl (—OH), a carbonyl (RCOR'), a sulfide (e.g., RSR'), a phosphate (ROP(=O)(OH)$_2$), an azo (RNNR'), a cyanate (ROCN), an amine (e.g., primary, secondary, or tertiary), an imine (RC(=NH)R'), a nitrile (RCN), a pyridinyl (or pyridyl), a diamine, a triamine, an azide, a diimine, a triimine, an amide, a diimide, or an ether (ROR'); where each of R and R' is independently a hydrogen or a substituted or unsubstituted alkyl group, aryl group, alkenyl group, or a combination of these. Optional substituent functional groups are also described below. In some embodiments, the term substituted refers to a compound wherein each of more than one hydrogen is replaced by another functional group, such as a halogen group. For example, when the substituent is oxo (i.e., =O), then two hydrogens on the atom are replaced. The substituent group can be any substituent group described herein. For example, substituent groups can include one or more of a hydroxyl, an amino (e.g., primary, secondary, or tertiary), an aldehyde, a carboxylic acid, an ester, an amide, a ketone, nitro, an urea, a guanidine, cyano, fluoroalkyl (e.g., trifluoromethane), halo (e.g., fluoro), aryl (e.g., phenyl), heterocyclyl or heterocyclic group (i.e., cyclic group, e.g., aromatic (e.g., heteroaryl) or non-aromatic where the cyclic group has one or more heteroatoms), oxo, or combinations thereof. Combinations of substituents and/or variables are permissible provided that the substitutions do not significantly adversely affect synthesis or use of the compound.

As used herein, the term "derivative" refers to a compound wherein an atom or functional group is replaced by another atom or functional group (e.g., a substituent function group as also described below), including, but not limited to: a hydrogen, a halogen or halide, an alkyl, a cycloalkyl, an aryl, a heteroaryl, an acyl, an alkoxy, an alkenyl, an alkynyl, an alkylaryl, an arylene, a heteroarylene, an alkenylene, a cycloalkenylene, an alkynylene, a hydroxyl (—OH), a carbonyl (RCOR'), a sulfide (e.g., RSR'), a phosphate (ROP (=O)(OH)$_2$), an azo (RNNR'), a cyanate (ROCN), an amine (e.g., primary, secondary, or tertiary), an imine (RC(=NH) R'), a nitrile (RCN), a pyridinyl (or pyridyl), a diamine, a triamine, an azide, a diimine, a triimine, an amide, a diimide, or an ether (ROR'); where each of R and R' is independently a hydrogen or a substituted or unsubstituted alkyl group, aryl group, alkenyl group, or a combination of these. Optional substituent functional groups are also described below. Optionally, such as optionally in any of Aspects 1-47, the term "derivative" refers to a compound wherein one or two atoms or functional groups are independently replaced by another atom or functional group. Optionally, the term derivative does not refer to or include replacement of a chalcogen atom (S, Se) that is a member of a heterocyclic group. Optionally, and unless otherwise stated, the term derivative does not refer to or include replacement of a chalcogen atom (S, Se) nor a N (nitrogen) where the chalcogen atom and the N are members same heterocyclic group. Optionally, but not necessarily, the term derivative does not include breaking a ring structure, replacement of a ring member, or removal of a ring member.

As is customary and well known in the art, hydrogen atoms in formula, are not always explicitly shown, for example, hydrogen atoms bonded to the carbon atoms of aromatic, heteroaromatic, and alicyclic rings are not always explicitly shown. The structures provided herein, for example in the context of the description of formula and schematics and structures in the drawings, are intended to convey to one of reasonable skill in the art the chemical composition of compounds of the methods and compositions of the invention, and as will be understood by one of skill in the art, the structures provided do not indicate the specific positions and/or orientations of atoms and the corresponding bond angles between atoms of these compounds.

As used herein, the terms "alkylene" and "alkylene group" are used synonymously and refer to a divalent group derived from an alkyl group as defined herein. The invention includes compounds having one or more alkylene groups. Alkylene groups in some compounds function as linking and/or spacer groups. Compounds of the invention may have substituted and/or unsubstituted $C_1$-$C_{20}$ alkylene, $C_1$-$C_{10}$ alkylene and $C_1$-$C_5$ alkylene groups, for example, as one or more linking groups (e.g. $L^1$-$L^6$).

As used herein, the terms "cycloalkylene" and "cycloalkylene group" are used synonymously and refer to a divalent group derived from a cycloalkyl group as defined herein. The invention includes compounds having one or more cycloalkylene groups. Cycloalkyl groups in some compounds function as linking and/or spacer groups. Compounds of the invention may have substituted and/or unsubstituted $C_3$-$C_{20}$ cycloalkylene, $C_3$-$C_{10}$ cycloalkylene and $C_3$-$C_5$ cycloalkylene groups, for example, as one or more linking groups (e.g. $L^1$-$L^6$).

As used herein, the terms "arylene" and "arylene group" are used synonymously and refer to a divalent group derived from an aryl group as defined herein. The invention includes compounds having one or more arylene groups. In some embodiments, an arylene is a divalent group derived from an aryl group by removal of hydrogen atoms from two intra-ring carbon atoms of an aromatic ring of the aryl group. Arylene groups in some compounds function as linking and/or spacer groups. Arylene groups in some compounds function as chromophore, fluorophore, aromatic antenna, dye and/or imaging groups. Compounds of the invention include substituted and/or unsubstituted $C_3$-$C_{30}$ arylene, $C_3$-$C_{20}$ arylene, $C_3$-$C_{10}$ arylene and $C_1$-$C_5$ arylene groups, for example, as one or more linking groups (e.g. $L^1$-$L^6$).

As used herein, the terms "heteroarylene" and "heteroarylene group" are used synonymously and refer to a divalent group derived from a heteroaryl group as defined herein. The invention includes compounds having one or more heteroarylene groups. In an embodiment, a heteroarylene is a divalent group derived from a heteroaryl group by removal of hydrogen atoms from two intra-ring carbon atoms or intra-ring nitrogen atoms of a heteroaromatic or aromatic ring of the heteroaryl group. Heteroarylene groups in some compounds function as linking and/or spacer groups. Heteroarylene groups in some compounds function as chromophore, aromatic antenna, fluorophore, dye and/or imaging groups. Compounds of the invention include substituted and/or unsubstituted $C_3$-$C_{30}$ heteroarylene, $C_3$-$C_{20}$ heteroarylene, $C_1$-$C_{10}$ heteroarylene and $C_3$-$C_5$ heteroarylene groups, for example, as one or more linking groups (e.g. $L^1$-$L^6$).

As used herein, the terms "alkenylene" and "alkenylene group" are used synonymously and refer to a divalent group derived from an alkenyl group as defined herein. The invention includes compounds having one or more alkenylene groups. Alkenylene groups in some compounds function as linking and/or spacer groups. Compounds of the invention include substituted and/or unsubstituted $C_2$-$C_{20}$ alkenylene, $C_2$-$C_{10}$ alkenylene and $C_2$-$C_5$ alkenylene groups, for example, as one or more linking groups (e.g. $L^1$-$L^6$).

As used herein, the terms "cylcoalkenylene" and "cylcoalkenylene group" are used synonymously and refer to a divalent group derived from a cylcoalkenyl group as defined herein. The invention includes compounds having one or more cylcoalkenylene groups. Cycloalkenylene groups in some compounds function as linking and/or spacer groups. Compounds of the invention include substituted and/or unsubstituted $C_3$-$C_{20}$ cylcoalkenylene, $C_3$-$C_{10}$ cylcoalkenylene and $C_3$-$C_5$ cylcoalkenylene groups, for example, as one or more linking groups (e.g. $L^1$-$L^6$).

As used herein, the terms "alkynylene" and "alkynylene group" are used synonymously and refer to a divalent group derived from an alkynyl group as defined herein. The invention includes compounds having one or more alkynylene groups. Alkynylene groups in some compounds function as linking and/or spacer groups. Compounds of the invention include substituted and/or unsubstituted $C_2$-$C_{20}$ alkynylene, $C_2$-$C_{10}$ alkynylene and $C_2$-$C_5$ alkynylene groups, for example, as one or more linking groups (e.g. $L^1$-$L^6$).

As used herein, the term "halo" refers to a halogen group such as a fluoro (—F), chloro (—Cl), bromo (—Br), iodo (—I) or astato (—At).

The term "heterocyclic" refers to ring structures containing at least one other kind of atom, in addition to carbon, in the ring. Examples of such heteroatoms include nitrogen, oxygen and sulfur. Heterocyclic rings include heterocyclic alicyclic rings and heterocyclic aromatic rings. Examples of heterocyclic rings include, but are not limited to, pyrrolidinyl, piperidyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl and tetrazolyl groups. Atoms of heterocyclic rings can be bonded to a wide range of other atoms and functional groups, for example, provided as substituents.

The term "carbocyclic" refers to ring structures containing only carbon atoms in the ring. Carbon atoms of carbocyclic rings can be bonded to a wide range of other atoms and functional groups, for example, provided as substituents.

The term "alicyclic ring" refers to a ring, or plurality of fused rings, that is not an aromatic ring. Alicyclic rings include both carbocyclic and heterocyclic rings.

The term "aromatic ring" refers to a ring, or a plurality of fused rings, that includes at least one aromatic ring group. The term aromatic ring includes aromatic rings comprising carbon, hydrogen and heteroatoms. Aromatic ring includes carbocyclic and heterocyclic aromatic rings. Aromatic rings are components of aryl groups.

The term "fused ring" or "fused ring structure" refers to a plurality of alicyclic and/or aromatic rings provided in a fused ring configuration, such as fused rings that share at least two intra ring carbon atoms and/or heteroatoms.

As used herein, the term "alkoxyalkyl" refers to a substituent of the formula alkyl-O-alkyl.

As used herein, the term "polyhydroxyalkyl" refers to a substituent having from 2 to 12 carbon atoms and from 2 to 5 hydroxyl groups, such as the 2,3-dihydroxypropyl, 2,3,4-trihydroxybutyl or 2,3,4,5-tetrahydroxypentyl residue.

As used herein, the term "polyalkoxyalkyl" refers to a substituent of the formula alkyl-(alkoxy)$_n$-alkoxy wherein n is an integer from 1 to 10, preferably 1 to 4, and more preferably for some embodiments 1 to 3.

Amino acids include glycine, alanine, valine, leucine, isoleucine, methionine, proline, phenylalanine, tryptophan, asparagine, glutamine, glycine, serine, threonine, serine, rhreonine, asparagine, glutamine, tyrosine, cysteine, lysine, arginine, histidine, aspartic acid and glutamic acid. As used herein, reference to "a side chain residue of a natural α-amino acid" specifically includes the side chains of the above-referenced amino acids. Peptides and peptide moieties, as used and described herein, comprise two or more amino acid groups connected via peptide bonds.

Amino acids and amino acid groups refer to naturally-occurring amino acids, unnatural (non-naturally occurring) amino acids, and/or combinations of these. Naturally-occurring amino acids are those encoded by the genetic code, as well as those amino acids that are later modified, e.g., hydroxyproline, γ-carboxyglutamate, and O-phosphoserine. Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of a naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Unnatural (non-naturally occurring) amino acids include, without limitation, amino acid analogs, amino acid mimetics, synthetic amino acids, N-substituted glycines, and N-methyl amino acids in either the L- or D-configuration that function in a manner similar to the naturally-occurring amino acids. For example, "amino acid analogs" can be unnatural amino acids that have the same basic chemical structure as naturally-occurring amino acids (i.e., a carbon that is bonded to a hydrogen, a carboxyl group, an amino group) but have modified side-chain groups or modified peptide backbones, e.g., homoserine, norleucine, methionine sulfoxide, methionine methyl sulfonium. "Amino acid mimetics" refer to chemical compounds that have a structure that is different from the general chemical structure of an amino acid, but that functions in a manner similar to a naturally-occurring amino acid. Amino acids may be referred to herein by either the commonly known three letter symbols or by the one-letter symbols recommended by the IUPAC-IUB Biochemical Nomenclature Commission.

The terms "monomer unit," "repeating monomer unit," "repeating unit," and "polymerized monomer" can be used interchangeably and refer to a monomeric portion of a polymer described herein which is derived from or is a product of polymerization of one individual "monomer" or "polymerizable monomer." Each individual monomer unit of a polymer is derived from or is a product of polymerization of one polymerizable monomer. Each individual "monomer unit" or "repeating unit" of a polymer comprises one (polymerized) polymer backbone group. For example, in a polymer that comprises monomer units X and Y arranged as X-Y-X-Y-X-Y-X-Y (where each X is identical to each other X and each Y is identical to each other Y), each X and each Y is independently can be referred to as a repeating unit or monomer unit.

Alkyl groups include straight-chain, branched and cyclic alkyl groups. Alkyl groups include those having from 1 to 30 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-30 carbon atoms.

The term cycloalkyl specifically refers to an alky group having a ring structure such as ring structure comprising 3-30 carbon atoms, optionally 3-20 carbon atoms and optionally 2-10 carbon atoms, including an alkyl group having one or more rings. Cycloalkyl groups include those having a 3-, 4-, 5-, 6-, 7-, 8-, 9- or 10-member carbon ring(s) and particularly those having a 3-, 4-, 5-, 6-, 7-, or 8-member ring(s). The carbon rings in cycloalkyl groups can also carry alkyl groups. Cycloalkyl groups can include bicyclic and tricycloalkyl groups. Alkyl groups are optionally substituted. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups, such as alkyl groups having one or more hydrogens replaced with one or more fluorine atoms. An alkoxy group is an alkyl group that has been modified by linkage to oxygen and can be represented by the formula R—O and can also be referred to as an alkyl ether group. Examples of alkoxy groups include, but are not limited to, methoxy, ethoxy, propoxy, butoxy and heptoxy. Alkoxy groups include substituted alkoxy groups wherein the alky portion of the groups is substituted as provided herein in connection with the description of alkyl groups. As used herein MeO— refers to $CH_3O$—. Compositions of some embodiments of the invention comprise alkyl groups as terminating groups, such as polymer backbone terminating groups and/or polymer side chain terminating groups. Substituted alkyl groups may include substitution to incorporate one or more silyl groups, for example wherein one or more carbons are replaced by Si.

Alkenyl groups include straight-chain, branched and cyclic alkenyl groups. Alkenyl groups include those having 1, 2 or more double bonds and those in which two or more of the double bonds are conjugated double bonds. Alkenyl groups include those having from 2 to 20 carbon atoms. Alkenyl groups include small alkenyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cycloalkenyl groups include those in which a double bond is in the ring or in an alkenyl group attached to a ring. The term cycloalkenyl specifically refers to an alkenyl group having a ring structure, including an alkenyl group having a 3-, 4-, 5-, 6-, 7-, 8-, 9- or 10-member carbon ring(s) and particularly those having a 3-, 4-, 5-, 6- or 7-member ring(s). The carbon rings in cycloalkenyl groups can also carry alkyl groups. Cycloalkenyl groups can include bicyclic and tricyclic alkenyl groups. Alkenyl groups are optionally substituted. Substituted alkenyl groups include among others those which are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted. Substituted alkenyl groups include fully halogenated or semihalogenated alkenyl groups, such as alkenyl groups having one or more hydrogens replaced with one or more fluorine atoms, chlorine atoms, bromine atoms and/or iodine atoms. Substituted alkenyl groups include fully fluorinated or semifluorinated alkenyl groups, such as alkenyl groups having one or more hydrogen atoms replaced with one or more fluorine atoms. Compositions of some embodiments of the invention comprise alkenyl groups as terminating groups, such as polymer backbone terminating groups and/or polymer side chain terminating groups.

Aryl groups include groups having one or more 5-, 6-7-, or 8-member aromatic rings, including heterocyclic aromatic rings. The term heteroaryl specifically refers to aryl groups having at least one 5-, 6-7-, or 8-member heterocyclic aromatic rings. Aryl groups can contain one or more fused aromatic rings, including one or more fused heteroaromatic rings, and/or a combination of one or more aromatic rings and one or more nonaromatic rings that may be fused or linked via covalent bonds. Heterocyclic aromatic rings can include one or more N, O, or S atoms in the ring. Heterocyclic aromatic rings can include those with one, two or three N atoms, those with one or two O atoms, and those with one or two S atoms, or combinations of one or two or three N, O or S atoms. Aryl groups are optionally substituted. Substituted aryl groups include among others those that are substituted with alkyl or alkenyl groups, which groups in turn can be optionally substituted. Specific aryl groups include phenyl, biphenyl groups, pyrrolidinyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms. Aryl groups include, but are not limited to, aromatic group-containing or heterocyclic aromatic group-containing groups corresponding to any one of the following: benzene, naphthalene, naphthoquinone, diphenylmethane, fluorene, anthracene, anthraquinone, phenanthrene, tetracene, tetracenedione, pyridine, quinoline, isoquinoline, indoles, isoindole, pyrrole, imidazole, oxazole, thiazole, pyrazole, pyrazine, pyrimidine, purine, benzimidazole, furans, benzofuran, dibenzofuran, carbazole, acridine, acridone, phenanthridine, thiophene, benzothiophene, dibenzothiophene, xanthene, xanthone, flavone, coumarin, azulene or anthracycline. As used herein, a group corresponding to the groups listed above expressly includes an aromatic or heterocyclic aromatic group, including monovalent, divalent and polyvalent groups, of the aromatic and heterocyclic aromatic groups listed herein are provided in a covalently bonded configuration in the compounds of the invention at any suitable point of attachment. In embodiments, aryl groups contain between 5 and 30 carbon atoms. In embodiments, aryl groups contain one aromatic or heteroaromatic six-member ring and one or more additional five- or six-member aromatic or heteroaromatic ring. In embodiments, aryl groups contain between five and eighteen carbon atoms in the rings. Aryl groups optionally have one or more aromatic rings or heterocyclic aromatic rings having one or more electron donating groups, electron withdrawing groups and/or targeting ligands provided as substituents. Compositions of some embodiments of the invention comprise aryl groups as terminating groups, such as polymer backbone terminating groups and/or polymer side chain terminating groups.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups. Alkylaryl groups are alternatively described as aryl groups substituted with one or more alkyl groups wherein the alkyl groups optionally carry additional substituents and the aryl groups are optionally substituted. Specific alkylaryl groups are alkyl-substituted phenyl groups such as methylphenyl. Substituted arylalkyl groups include fully halogenated or semihalogenated arylalkyl groups, such as arylalkyl groups having one or more alkyl and/or aryl groups having one or more hydrogens replaced with one or more fluorine atoms, chlorine atoms, bromine atoms and/or iodine atoms. Compositions of some embodiments of the invention comprise arylalkyl groups as terminating groups, such as polymer backbone terminating groups and/or polymer side chain terminating groups.

As to any of the groups described herein which contain one or more substituents, it is understood that such groups do not contain any substitution or substitution patterns which are sterically impractical and/or synthetically non-feasible. In addition, the compounds of this invention include all stereochemical isomers arising from the substitution of these compounds. Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for any alkyl, alkenyl and aryl group includes substitution with one or more of the following substituents, among others:

halogen, including fluorine, chlorine, bromine or iodine; pseudohalides, including —CN;
—COOR where R is a hydrogen or an alkyl group or an aryl group and more specifically where R is a methyl, ethyl, propyl, butyl, or phenyl group all of which groups are optionally substituted;
—COR where R is a hydrogen or an alkyl group or an aryl group and more specifically where R is a methyl, ethyl, propyl, butyl, or phenyl group all of which groups are optionally substituted;
—CON(R)$_2$ where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;
—OCON(R)$_2$ where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;
—N(R)$_2$ where each R, independently of each other R, is a hydrogen, or an alkyl group, or an acyl group or an aryl group and more specifically where R is a methyl, ethyl, propyl, butyl, phenyl or acetyl group, all of which are optionally substituted; and where R and R can form a ring which can contain one or more double bonds and can contain one or more additional carbon atoms;
—SR, where R is hydrogen or an alkyl group or an aryl group and more specifically where R is hydrogen, methyl, ethyl, propyl, butyl, or a phenyl group, which are optionally substituted;
—SO$_2$R, or —SOR where R is an alkyl group or an aryl group and more specifically where R is a methyl, ethyl, propyl, butyl, or phenyl group, all of which are optionally substituted;
—OCOOR where R is an alkyl group or an aryl group;
—SO$_2$N(R)$_2$ where each R, independently of each other R, is a hydrogen, or an alkyl group, or an aryl group all of which are optionally substituted and wherein R and R can form a ring which can contain one or more double bonds and can contain one or more additional carbon atoms; and
—OR where R is H, an alkyl group, an aryl group, or an acyl group all of which are optionally substituted. In a particular example R can be an acyl yielding —OCOR" where R" is a hydrogen or an alkyl group or an aryl group and more specifically where R" is methyl, ethyl, propyl, butyl, or phenyl groups all of which groups are optionally substituted.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups; and methoxyphenyl groups, particularly 4-methoxyphenyl groups.

As to any of the above groups which contain one or more substituents, it is understood that such groups do not contain any substitution or substitution patterns which are sterically impractical and/or synthetically non-feasible.

Many of the molecules disclosed herein contain one or more ionizable groups. Ionizable groups include groups from which a proton can be removed (e.g., —COOH) or added (e.g., amines) and groups that can be quaternized (e.g., amines). All possible ionic forms of such molecules and salts thereof are intended to be included individually in the disclosure herein. With regard to salts of the compounds herein, one of ordinary skill in the art can select from among a wide variety of available counterions that are appropriate for preparation of salts of this invention for a given application. In specific applications, the selection of a given anion or cation for preparation of a salt can result in increased or decreased solubility of that salt.

The compounds of this invention can contain one or more chiral centers. Accordingly, this invention is intended to include racemic mixtures, diastereomers, enantiomers, tautomers and mixtures enriched in one or more stereoisomer. The scope of the invention as described and claimed encompasses the racemic forms of the compounds as well as the individual enantiomers and non-racemic mixtures thereof.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another. It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}$H), iodine-125 ($^{125}$I), or carbon-14 ($^{14}$C). All isotopic variations of the compounds of the present invention, whether radioactive or not, are encompassed within the scope of the present invention.

The symbol "$\sim\!\!\sim$" denotes the point of attachment of a chemical moiety, functional group, atom, ion, unpaired electron, or other chemical species to the represented molecule, compound, or chemical formula. For example, in the formula

"X" represents a molecule or compound, the symbol $\sim\!\!\sim$ denotes a point of attachment of a chemical moiety, functional group, atom, ion, unpaired electron, or other chemical species to X (where X corresponds to the represented molecule, compound, or chemical formula) via covalent bonding. As used herein, the various functional groups represented will be understood to have a point of attachment at the functional group having the hyphen or dash (-) or a dash used in combination with an asterisk (*). In other words, in the case of —CH$_2$CH$_2$CH$_3$ or —CH$_2$CH$_2$CH$_3$, it will be understood that the point of attachment is the CH$_2$ group at the far left. If a group is recited without an asterisk or a dash, then the attachment point is indicated by the plain and ordinary meaning of the recited group.

Where substituent groups are specified by their conventional chemical formulae, written from left to right, they equally encompass the chemically identical substituents that would result from writing the structure from right to left, e.g., —CH$_2$O— is equivalent to —OCH$_2$—.

Additional embodiments and descriptions may be found in U.S. Provisional Patent Application 62/928,129, filed Oct. 30, 2019, U.S. Provisional Patent Application No. 62/868,369, filed Jun. 28, 2019, Huang, et al. (Huang, Y.; Li, Y.; Hu, Z.; Yue, X.; Proetto, M. T.; Jones, Y.; Gianneschi, N. C., Mimicking Melanosomes: Polydopamine Nanoparticles as Artificial Microparasols. ACS Cent Sci 2017, 3 (6), 564-569), and US Patent Publication No. 2020/0113934A1, all of which are incorporated herein in their entirety to the extent not inconsistent herewith.

In an embodiment, a composition or compound of the invention, such as an alloy or precursor to an alloy, is isolated or substantially purified. In an embodiment, an isolated or purified compound is at least partially isolated or substantially purified as would be understood in the art. In an embodiment, a substantially purified composition, compound or formulation of the invention has a chemical purity of 95%, optionally for some applications 99%, optionally for some applications 99.9%, optionally for some applications 99.99%, and optionally for some applications 99.999% pure.

DETAILED DESCRIPTION OF THE INVENTION

In the following description, numerous specific details of the devices, device components and methods of the present invention are set forth in order to provide a thorough explanation of the precise nature of the invention. It will be apparent, however, to those of skill in the art that the invention can be practiced without these specific details.

Included herein are method for treating hair, such as to dye hair, using viscous solutions that comprise one or more solution-thickening agents together with one or more artificial melanin precursors and/or one or more artificial melanin materials. The hair treatment occurs when hair is contacted with the viscous solution in the presence of an oxidizing agent.

The purpose of using thickeners is to make the hair dying formula (the "viscous solution") more viscous for easy application to the hair. With a viscous solution, less of the artificial melanin dye will run off allowing for a larger possibility of the melanin monomer to adhere to the hair and polymerize. Various solution-thickening agents are contemplated, including but not limited to those described in the below Examples.

Non-Limiting Examples

The following solution-thickening agents are described in these Examples: Hyaluronic Acid, Xanthan Gum, *Sclerotium* Gum, Hydroxyethylcellulose, and Cetearyl Alcohol.

In exemplary aspects, initially a solution of 5 mg/mL of each of the thickeners were made in water. Cetearyl alcohol did not dissolve in water, so was not used in further hair dye experiments. Dopamine at 5 mg/mL and 6% NH$_4$OH were added to the solutions of hyaluronic acid, xanthan gum, *Sclerotium* gum, and hydroxyethylcellulose to make sure dopamine polymerized in each of these solutions. The dopamine was able to polymerize but did not form discrete particles as it does just in water (FIGS. 1A-1D).

In exemplary aspects, for the thickeners, instead of submerging hair in a water bath as done previously, hair can be coated with a thickener and along with the dye and could be left at room temperature or placed in a heated humid environment at 40° C. (FIG. 2). Solutions of 10 mg/mL of dopamine and hyaluronic acid can be prepared in water. Thickeners were sonicated for at least one hour to completely dissolved in water. 5 mL of 10 mg/mL of thickener and 5 mL of 10 mg/mL of dopamine can be combined and stirred in a dish. 6% or 3% of $NH_4OH$ can be added to the thickener/dopamine solution; more of the base will cause the reaction to proceed faster and the hair to be darker. The dopamine will immediately start to polymerize. The hair can then be coated in the solution. Thickener will make the solution more viscous, which allow for the hair to be coated more evenly and increase amount of solution adhered to the hair. The hair can then be placed on a dish and placed into an insulated water bath heated to 40° C. for two hours or left at room temperature. Once hair dyeing is done, the hair can be washed with shampoo and water.

Figure 3:
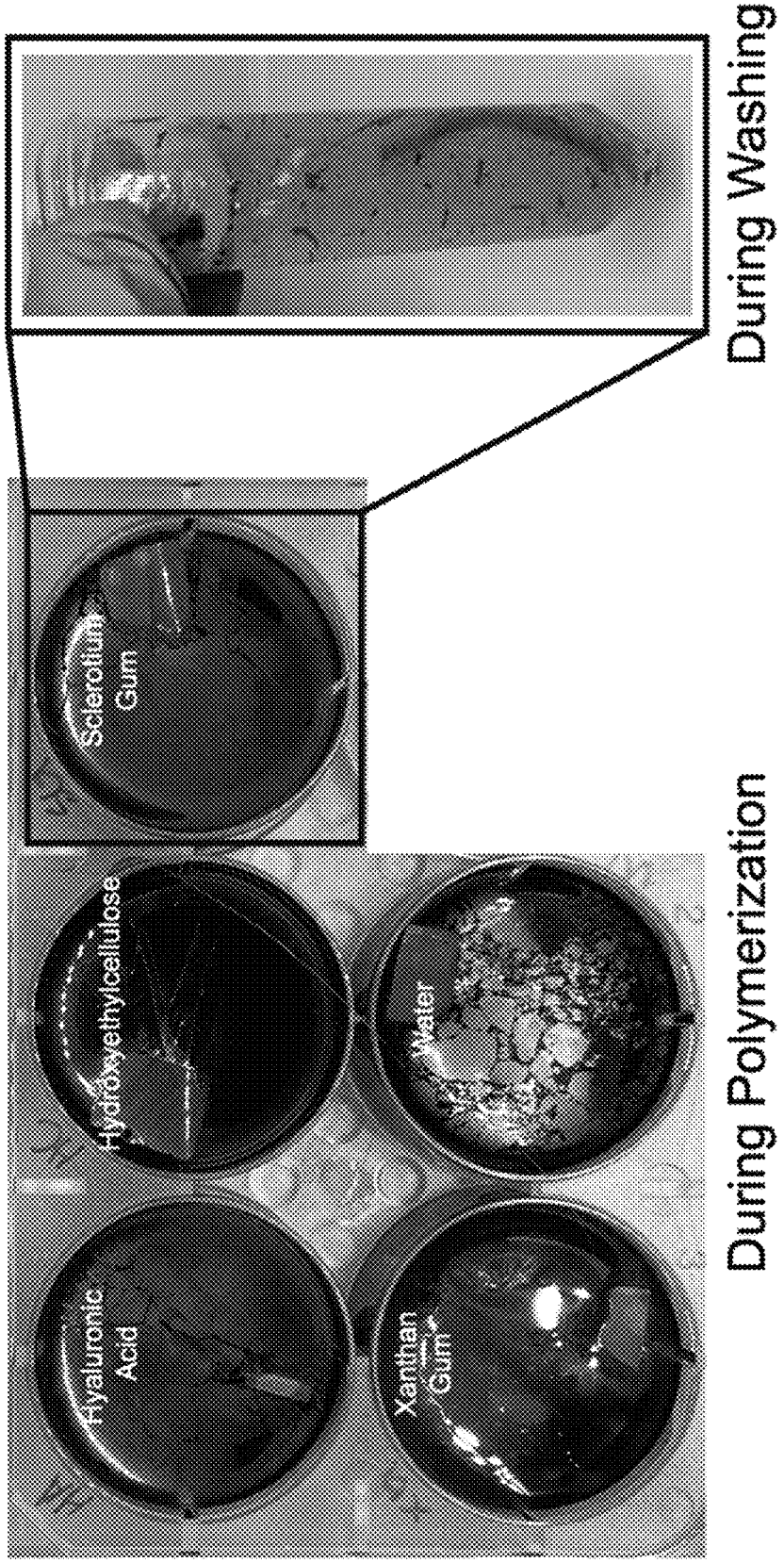
FIG. 3: 5 mg/mL of dopamine polymerized in water or 5 mg/mL of the following thickeners and 3% $NH_4OH$: hyaluronic acid, hydroxyethylcellulose, *Sclerotium* gum, xanthan gum. The solution was heated to 40° C. The polymerization was left to go for two hours before the hair was washed with water and shampoo. During washing evidence of the formation of film with dopamine and the thickeners shown, as the film flakes off of the hair.

In exemplary aspects, during the polymerization with xanthan gum, *Sclerotium* gum, and hydroxyethylcellulose the dopamine preferred to adhere to the hydrogel formed rather than the hair (FIG. 3). A film was formed with the dopamine and hydrogel that encased the hair but once washed this film came off and the hair looked similar to the control. Only with hyaluronic acid was the hair dyed significantly darker. The hydroxyethylcellulose also managed to dye the hair darker, but there was evidence of a film forming as well.

Solution thickening agents such as hyaluronic acid may also be used to make hair treatment solutions viscous when amines are included in the hair treatment solution. For example, solutions of 10 mg/mL of dopamine and hyaluronic acid can be prepared in water. Hyaluronic may be sonicated for at least one hour for it to be completely dissolved in water. 5 mL of 10 mg/mL hyaluronic acid and 5 mL of 10 mg/mL of dopamine can be combined and stirred in a dish. 1.5 mL of one of the amines, aminomethyl proponal, aminopropanol, or dimethyaminomethyl proponal, can be added to the hyaluronic/dopamine solution. The dopamine will immediately start to polymerize. The hair can then be coated in the solution. Hyaluronic acid will make the solution more viscous, which allow for the hair to be coated more evenly and increase amount of solution adhered to the hair. The hair can then be placed on a dish and placed into an insulated water bath heated to 40° C. for two hours. Once hair dyeing is done, the hair can be washed with shampoo and water.

Certain Aspects and Embodiments

Various aspects are contemplated herein, several of which are set forth in the paragraphs below. It is explicitly contemplated and disclosed herein that any aspect or portion thereof can be combined to form an aspect. Moreover, for example, the term "any preceding aspect" means any aspect that appears prior to the aspect that contains such phrase is referenced (for example, the clause "Aspect 10: the method of any preceding aspect . . . " means that any aspect prior to Aspect 10 is referenced, including Aspects 1-9). Further, for example, the term "any preceding and/or following Aspect" means any Aspect that appears prior to or after the Aspect that contains such phrase is referenced (for example, the clause "Aspect 10: the method of any preceding and/or following Aspect . . . " means that any aspect prior to Aspect 10 is referenced, including Aspects 1-9, as well as any Aspect after Aspect 10, including Aspects 11-47). In addition, it is explicitly contemplated and disclosed herein that any reference to Aspect X, where X is an integer corresponding to one of the below Aspects (e.g., Aspect 17), includes reference to Aspects Xa, Xb, and/or Xc, if present, etc. (e.g., Aspect 17a, Aspect 17b, and/or Aspect 17c, etc.).

Aspect 1a: A method of treating hair of a subject with one or more artificial melanin materials, the method comprising:

contacting, in a viscous solution, one or more artificial melanin precursors with an oxidizing agent in the presence of a solution-thickening agent and the hair of said subject to form said one or more artificial melanin material;

wherein said one or more artificial melanin materials associates with said hair of said subject, thereby treating the hair of said subject.

Aspect 1b: A method of treating hair of a subject with one or more artificial melanin materials, the method comprising:

contacting one or more artificial melanin precursors with an oxidizing agent in the presence of a solution-thickening agent and the hair of said subject to form said one or more artificial melanin material (the one or more artificial melanin precursors optionally being in a viscous solution, optionally the viscous solution comprising the one or more artificial melanin precursors and the solution-thickening agent);

wherein said one or more artificial melanin materials associates with said hair of said subject, thereby treating the hair of said subject.

Aspect 2a: The method of any preceding and/or following Aspects, wherein during the step of contacting the viscous solution is characterized by a viscosity selected from the range of 0.5 cP to 500 cP. Aspect 2b: The method of any preceding and/or following Aspects, wherein during the step of contacting the viscous solution is characterized by a viscosity selected from any range between 0.5 cP and 15000 cP at 25° C., such as, but not limited to, selected from the range of 0.5 cp to 500 cP, optionally 0.5 cp to 100 cP, optionally 5 cp to 15000 cP, optionally 5 cp to 1000 cP, optionally 5 cp to 5000 cP, optionally 10 cp to 1000 cP, optionally 10 cp to 5000 cP, optionally 1 cp to 8000 cP, optionally 50 cp to 10000 cP, optionally 5 cp to 15000 cP, optionally 20 cp to 15000 cP, optionally 50 cp to 15000 cP, optionally 100 cp to 15000 cP, optionally 150 cp to 15000 cP.

Aspect 3: The method of any preceding and/or following Aspect, wherein during the step of contacting a concentration of the solution-thickening in the viscous solution is selected from the range of 0.5 mg/mL to 10 mg/mL.

Aspect 4: The method of any preceding and/or following Aspect, wherein the solution-thickening agent comprises hydrogel and/or a hydrogel precursor.

Aspect 5: The method of any preceding and/or following Aspect, wherein the solution-thickening agent is characterized as a polysaccharide comprising repeating saccharide units, each saccharide repeating unit comprising at least one amine group.

Aspect 6: The method of Aspect 5, wherein each repeating saccharide unit is a disaccharide.

Aspect 7: The method of any preceding and/or following Aspect, wherein the solution-thickening agent is characterized as a glycosaminoglycans.

Aspect 8: The method of any preceding and/or following Aspect, wherein the solution-thickening agent is characterized by formula FX1a or FX1b:

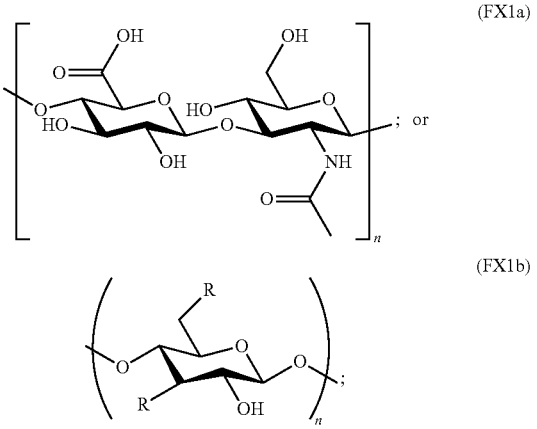

wherein:

n is an integer and the solution-thickening agent is characterized by molecular weight selected from the range of 90-6,000 kDA, and wherein each R is independently —OH, —COOH, —CH$_3$O, —CHCHCOOCH$_3$, or —NHCOCH$_3$.

Aspect 9: The method of any preceding and/or following Aspect, wherein the solution-thickening agent comprises hyaluronic acid and/or hydroxyethylcellulose.

Aspect 10: The method of any preceding and/or following Aspect, wherein the solution-thickening agent comprises hyaluronic acid or a derivative thereof.

Aspect 11: The method of any preceding and/or following Aspect, wherein the solution-thickening agent comprises hyaluronic acid.

Aspect 12: The method of any preceding and/or following Aspect, wherein the solution-thickening agent comprises a combination of a plurality of different solution-thickening agents.

Aspect 13: The method of any preceding and/or following Aspect, wherein the solution-thickening agent is not chemically associated (e.g., not covalently bonded) with the one or more artificial melanin precursors and/or with the one or more artificial melanin materials during and after the step of contacting, for example, wherein the solution-thickening agent only undergoes noncovalent interactions (e.g., ionic association, dipole-dipole interactions, hydrogen bonding, etc.) with the artificial melanin precursors and/or with the one or more artificial melanin materials.

Aspect 14: The method of any preceding and/or following Aspect, wherein the treated hair after the step of contacting is dyed directly by the one or more artificial melanin materials.

Aspect 15: The method of any preceding and/or following Aspect comprising a step of preparing the viscous solution having the one or more artificial melanin precursors and the solution-thickening agent prior to the step of contacting.

Aspect 16: The method of Aspect 15, wherein the step of preparing comprises combining the one or more artificial melanin precursors, the solution-thickening agent, and one or more alkaline agents and/or one or more enzymes in water.

Aspect 17a: The method of any preceding and/or following Aspect, wherein the one or more artificial melanin precursors polymerize in the presence of the solution-thickening agent prior to the step of contacting. Aspect 17b: The method of any preceding and/or following Aspect, wherein a portion of the one or more artificial melanin precursors polymerize in the presence of the solution-thickening agent prior to the step of contacting. Aspect 17c: The method of any preceding and/or following Aspect, wherein at least a portion of the one or more artificial melanin precursors polymerize in the presence of the solution-thickening agent during the step of contacting.

Aspect 18: The method of any preceding and/or following Aspect, wherein the step of contacting comprises applying the viscous solution to the hair and subsequently resting the hair (which is in contact with the viscous solution) for a time.

Aspect 19a: The method of Aspect 18, wherein at least a portion of the hair, which is in contact with the viscous solution, is submerged in water or an aqueous solution during at least a portion of the step of resting.

Aspect 20: The method of Aspect 18 or 19, wherein at least a portion of the hair, which is in contact with the viscous solution, is exposed to humid air having a relative humidity of greater than 30% during at least a portion of the step of resting.

Aspect 21: The method of any preceding and/or following Aspect further comprising removing (e.g., washing and/or rinsing) the viscous solution from the hair after the step of contacting.

Aspect 22: The method of Aspect 21, wherein the treated hair comprises the artificial melanin material associated therewith after the viscous solution is removed.

Aspect 23: The method of any preceding and/or following Aspect, wherein said one or more artificial melanin materials chemically associate with said hair of said subject.

Aspect 24: The method of any preceding and/or following Aspect, wherein said one or more artificial melanin materials associate directly with the hair.

Aspect 25: The method of any preceding and/or following Aspect, wherein the association between said one or more artificial melanin materials and the hair comprises chemical bonding, for example, a mixture of covalent and ionic binding, wherein such covalent binding can optionally be through a Michael-type addition and/or Schiff-base formation and ionic binding can optionally be through hydrogen-binding or pi-pi interactions.

Aspect 26a: The method of any preceding and/or following Aspect, wherein the one or more artificial melanin precursors comprise substituted or unsubstituted: dopamine monomers, 1,8-dihydroxynaphthalene or its derivative, tyrosine monomers, tyramine monomers, amino acids, phenolamines, catecholamines, or any combination of these. Aspect 26b: The method of any preceding and/or following Aspect, wherein the one or more artificial melanin precursors comprise one or more polymerization products of any of species provided in Aspect 26a.

Aspect 27a: The method of any preceding and/or following Aspect, wherein the viscous solution further comprises polymerized artificial melanin precursors immediately prior to and/or during the step of contacting. Aspect 27b: The method of any preceding and/or following Aspect, wherein the viscous solution further comprises polymerized artificial melanin precursors immediately during the step of contacting.

Aspect 28: The method of any preceding and/or following Aspect, wherein the step of contacting is performed further in the presence of one or more alkaline agents and/or one or more pH buffers.

Aspect 29: The method of any preceding and/or following Aspect, wherein the step of contacting is performed at a pH selected from the range of 8.5 to 14.

Aspect 30: The method of any preceding and/or following Aspect, wherein the step of contacting is performed at a temperature greater than or equal to 20° C.

Aspect 31a: The method of any preceding and/or following Aspect, wherein the step of contacting is performed at a temperature greater than or equal to 30° C. Aspect 31b: The method of any preceding and/or following Aspect, wherein the step of contacting is performed at a temperature selected from the range of 26° C. to 45° C., optionally 30° C. to 45° C., optionally 30° C. to 41° C.

Aspect 32a: The method of any preceding and/or following Aspect, wherein during the step of contacting the solution comprises a total concentration of the one or more artificial melanin precursors is selected from the range of 0.5 to 100 mg/mL. Aspect 32b: The method of any preceding and/or following Aspect, wherein during the step of contacting the solution comprises a total concentration of the one or more artificial melanin precursors is selected from the range of 0.5 to 2000 mg/mL, or any value or range therebetween, such as optionally 0.5 to 1000 mg/mL, optionally 1 to 1000 mg/mL, optionally 5 to 1000 mg/mL, optionally 0.5 to 500 mg/mL, optionally 1 to 500 mg/mL, optionally 0.5 to 200 mg/mL, optionally 1 to 200 mg/mL, optionally 1 to 100 mg/mL, optionally 5 to 100 mg/mL.

Aspect 33: The method of any preceding and/or following Aspect, wherein the solution further comprises a metal chelating agent.

Aspect 34: The method of any preceding and/or following Aspect, wherein the solution further comprises one or more enzymes.

Aspect 35: The method of any preceding and/or following Aspect, wherein the oxidizing agent comprises oxygen (e.g., oxygen in air), sodium periodate, potassium permanganate, ammonium persulfate, or any combination of these.

Aspect 36: The method of any preceding and/or following Aspect, wherein the one or more artificial melanin precursors are not bound to, conjugated to, attached to, coated by, encompassed by, or otherwise chemically associated with a natural or biological proteinaceous matrix, component, or lipid.

Aspect 37: The method of any preceding and/or following Aspect, wherein the artificial melanin material is in the form of nanoparticles associated with the hair.

Aspect 38: The method of any preceding and/or following Aspect, wherein at least a portion of the one or more artificial melanin precursors comprise one or more thiol-reactive moieties.

Aspect 39: The method of any preceding and/or following Aspect, wherein the artificial melanin material comprise a polymerization product of the one or more artificial melanin precursors at least a portion of which having one or more thiol-reactive moieties.

Aspect 40a: A method of treating hair of a subject with one or more artificial melanin materials, the method comprising:
contacting, in a viscous solution, one or more artificial melanin precursors and/or one or more artificial melanin materials with an oxidizing agent in the presence of a solution-thickening agent and the hair of said subject to form one or more other artificial melanin materials; wherein said one or more other artificial melanin materials associate with said hair of said subject, thereby treating the hair of said subject.

Aspect 40b: A method of treating hair of a subject with one or more artificial melanin materials, the method comprising:
contacting one or more artificial melanin precursors and/or one or more artificial melanin materials with an oxidizing agent in the presence of a solution-thickening agent and the hair of said subject to form one or more other artificial melanin materials (the one or more artificial melanin precursors optionally being in a viscous solution, optionally the viscous solution comprising the one or more artificial melanin precursors and/or the one or more artificial melanin materials and further the solution-thickening agent);
wherein said one or more other artificial melanin materials associate with said hair of said subject, thereby treating the hair of said subject.

Aspect 41: The method of Aspect 40 (i.e., Aspect 40a and/or Aspect 40b), wherein the one or more artificial melanin precursors and the one or more artificial melanin materials are not bound to, conjugated to, attached to, coated by, encompassed by, or otherwise chemically associated with a natural or biological proteinaceous matrix, component, or lipid.

Aspect 42: A viscous solution for hair treatment, the viscous solution comprises:
one or more artificial melanin precursors; and
one or more solution-thickening agents.

Aspect 43: A viscous solution for hair treatment, the viscous solution comprises:
one or more artificial melanin precursors and/or one or more artificial melanin materials; and
one or more solution-thickening agents.

Aspect 44: The solution of Aspect 42 or 43, wherein the solution comprises an oxidizing agent and/or wherein the solution is configured to treat hair in the presence of an oxidizing agent.

Aspect 45: The solution of any one of Aspects 42-44, wherein the artificial melanin precursors are configured to polymerize in the presence of an oxidizing agent.

Aspect 46: A composition of matter comprising the hair of said subject treated with said artificial melanin material generated by any of the methods according to any preceding and/or following Aspect.

Aspect 47: A composition of matter comprising hair of a subject having a coating of artificial melanin nanoparticles, wherein said coating of artificial melanin nanoparticles is characterized by nanostructures have size domains ranging from 5 nm to 500 nm; wherein said artificial melanin nanoparticles associate with said hair of said subject.

Certain Additional Aspects and Embodiments

Any of the methods disclosed herein, such as any of Aspects 1-41, may be carried out in a single step or in a series of steps. Optionally in any of the methods disclosed herein, such as optionally in any of Aspects 1-41, the artificial melanin precursors are contacted in a solution with an oxidizing agent in the presence of the hair at room temperature and then the temperature is subsequently raised to a temperature equal to or greater than 30° C. to provide for treatment of the hair. Optionally in any of the methods disclosed herein, such as optionally in any of Aspects 1-41, the artificial melanin precursors and oxidizing agent are contacted in solution in the presence of the hair at a temperature equal to or greater than 30° C. to provide for treatment of the hair.

Optionally in any of the methods disclosed herein, such as optionally in any of Aspects 1-41, the contacting step results in deposition of the artificial melanin material on the hair of the subject and/or uptake of the artificial melanin material into the hair of the subject. Optionally in any of the methods disclosed herein, such as optionally in any of Aspects 1-41, the contacting step results in covalent or noncovalent association of the artificial melanin material with the hair of the subject. Optionally in any of the methods disclosed herein, such as optionally in any of Aspects 1-41, the contacting step results in noncovalent association of the artificial melanin material with the hair of the subject. Optionally in any of the methods disclosed herein, such as optionally in any of Aspects 1-41, the contacting step results in covalent association of the artificial melanin material with the hair of the subject. Optionally in any of the methods disclosed herein, such as optionally in any of Aspects 1-41, the contacting step results in a change in the color of the hair of the subject. Optionally in any of the methods disclosed herein, such as optionally in any of Aspects 1-41, the change in the color of the hair of the subject remains persistent for at least a period of 5 weeks. Optionally in any of the methods disclosed herein, such as optionally in any of Aspects 1-41, the change in the color of the hair of the subject remains persistent for at least a period of one year. Optionally in any of the methods disclosed herein, such as optionally in any of Aspects 1-41, the change in the color of the hair of the subject remains persistent for at least 18 washing or rinsing cycles for the hair. Optionally in any of the methods disclosed herein, such as optionally in any of Aspects 1-41, the contacting step is carried out for a time selected from the range of 1 minute to 5 hours, optionally 15 minutes to 5 hours, optionally, 30 minutes to 5 hours, optionally 1 hour to 5 hours, optionally 2 hours to 5 hours.

The following describes exemplary embodiments of reaction conditions associated with methods and materials disclosed herein.

Optionally in any of the methods disclosed herein, such as optionally in any of Aspects 1-41, the contacting step is carried out in the absence of a metal chelating agent. Optionally in any of the methods disclosed herein, such as optionally in any of Aspects 1-41, the contacting step is carried out in the absence of a metal chelating agent. Optionally in any of the methods disclosed herein, such as optionally in any of Aspects 1-41, the solution is free of a metal chelating agent. Optionally in any of the methods disclosed herein, such as optionally in any of Aspects 1-41, the solution comprises a metal chelating agent having a concentration of less than or equal to 15 mM, optionally less than or equal to 10 mM, optionally less than or equal to 5 mM, optionally less than or equal to 1 mM. Optionally in any of the methods disclosed herein, such as optionally in any of Aspects 1-41, the metal chelating agent is an iron-containing chelating agent and/or a copper-containing chelating agent. Optionally in any of the methods disclosed herein, such as optionally in any of Aspects 1-41, the contacting step is carried out in the absence of a strong oxidizing condition. Optionally in any of the methods disclosed herein, such as optionally in any of Aspects 1-41, the contacting step is carried out in the absence of sodium periodate. Optionally in any of the methods disclosed herein, such as optionally in any of Aspects 1-41, the contacting step takes place under conditions providing for polymerization of the artificial melanin precursors to generate the artificial melanin material. Optionally in any of the methods disclosed herein, such as optionally in any of Aspects 1-41, the contacting step does not change the mechanical properties of the hair of said subject. Optionally in any of the methods disclosed herein, such as optionally in any of Aspects 1-41, the contacting step is carried out at the temperature ranging from 30° C. to 45° C. Optionally in any of the methods disclosed herein, such as optionally in any of Aspects 1-41, the contacting step is carried out at physiological temperature. Optionally in any of the methods disclosed herein, such as optionally in any of Aspects 1-41, especially but not necessarily any method comprising an enzyme-containing solution, the contacting step is carried out at a pH selected from the range of 4 to 10, optionally 5 to 9, optionally 6 to 8, optionally 6 to 9, optionally 5 to 8, preferably 6.5 to 7.5, preferably 6.7 to 7.3.

Optionally in any of the methods disclosed herein, such as optionally in any of Aspects 1-41, especially but not necessarily a method comprising an alkaline solution free of enzymes, the contacting step is carried out at pH greater than 7. Optionally in any of the methods disclosed herein, such as optionally in any of Aspects 1-41, especially but not necessarily a method comprising an alkaline solution free of enzymes, the contacting step is carried out at a pH selected from the range of 7 to 12. Optionally in any of the methods disclosed herein, such as optionally in any of Aspects 1-41, the solution is an alkaline. Optionally in any of the methods disclosed herein, such as optionally in any of Aspects 1-41, the solution is an ammonia solution, or a sodium hydroxide solution. Optionally in any of the methods disclosed herein, such as optionally in any of Aspects 1-41, the solution comprises ammonia or sodium hydroxide. Optionally in any of the methods disclosed herein, such as optionally in any of Aspects 1-41, the solution is a solution of monoethanolamine or a derivative thereof. Optionally in any of the methods disclosed herein, such as optionally in any of Aspects 1-41, the solution comprises a solution of monoethanolamine or a derivative thereof. Optionally in any of the methods disclosed herein, such as optionally in any of Aspects 1-41, the solution is an alkaline buffer solution. Optionally in any of the methods disclosed herein, such as optionally in any of Aspects 1-41, the solution comprises an alkaline buffer. Optionally in any of the methods disclosed herein, such as optionally in any of Aspects 1-41, the buffer solution is a tris(hydroxymethyl)aminomethane buffer solution. Optionally in any of the methods disclosed herein, such as optionally in any of Aspects 1-41, the solution is an ammonia solution having a concentration less than or equal to 10% (w/v). Optionally in any of the methods disclosed herein, such as optionally in any of Aspects 1-41, the solution comprises ammonia at a concentration less than or equal to 10% (w/v). Optionally in any of the methods disclosed herein, such as optionally in any of Aspects 1-41, the solution is an ammonia solution having a concentration selected over the range of 1 to 6% (w/v). Optionally in any of the methods disclosed herein, such as optionally in any of Aspects 1-41, the solution comprises ammonia at a concentration selected over the range of 1 to 6% (w/v). Optionally in any of the methods disclosed herein, such as optionally in any of Aspects 1-41, the solution is a sodium hydroxide solution having a concentration less than or equal to 0.1 N. Optionally in any of the methods disclosed herein, such as optionally in any of Aspects 1-41, the solution comprises sodium hydroxide having a concentration less than or equal to 0.1 N. Optionally in any of the methods disclosed herein, such as optionally in any of Aspects 1-41, the solution is a sodium hydroxide solution having a concentration less than or equal to 0.05 N. Optionally in any of the methods disclosed herein, such as optionally in any of Aspects 1-41, the solution comprises sodium hydroxide solution at a concentration less than or equal to 0.05 N. Optionally in any of the methods disclosed herein, such as optionally in any of Aspects 1-41, the solution is a sodium hydroxide solution having a concentration selected over the range of 0.01 N to 0.1 N. Optionally in any of the methods disclosed herein, such as optionally in any of Aspects 1-41, the solution comprises sodium hydroxide at a concentration selected over the range of 0.01 N to 0.1 N. Optionally in any of the methods disclosed herein, such as optionally in any of Aspects 1-41, the solution is a sodium hydroxide solution having a concentration selected over the range of 0.05 N to 0.1 N. Optionally in any of the methods disclosed herein, such as optionally in any of Aspects 1-41, the solution comprises sodium hydroxide at a concentration selected over the range of 0.05 N to 0.1 N. Optionally in any of the methods disclosed herein, such as optionally in any of Aspects 1-41, the solution is a tris(hydroxymethyl)aminomethane solution having a concentration less than or equal to 50 mM. Optionally in any of the methods disclosed herein, such as optionally in any of Aspects 1-41, the solution comprises tris(hydroxymethyl)aminomethane at a concentration less than or equal to 50 mM. Optionally in any of the methods disclosed herein, such as optionally in any of Aspects 1-41, the solution is a tris(hydroxymethyl)aminomethane solution having a concentration selected over the range of 1 mM to 50 mM. Optionally in any of the methods disclosed herein, such as optionally in any of Aspects 1-41, the solution comprises tris(hydroxymethyl)aminomethane at a concentration selected over the range of 1 mM to 50 mM. Optionally in any of the methods disclosed herein, such as optionally in any of Aspects 1-41, the solution is a tris(hydroxymethyl)aminomethane solution having a concentration selected over the range of 10 mM to 50 mM. Optionally in any of the methods disclosed herein, such as optionally in any of Aspects 1-41, the solution comprises tris(hydroxymethyl)aminomethane at a concentration selected over the range of 10 mM to 50 mM.

Optionally in any of the methods disclosed herein, such as optionally in any of Aspects 1-41, the solution is an enzyme containing solution comprising one or more enzymes. Generally, the one or more enzymes facilitate and participate in the formation of the artificial melanin material and/or facilitate the artificial melanin material associating with the hair of the subject. Optionally in any of the methods disclosed herein, such as optionally in any of Aspects 1-41, the one or more enzymes comprises one or more oxidoreductase enzymes. Optionally in any of the methods disclosed herein, such as optionally in any of Aspects 1-41, the one or more enzymes comprises tyrosinase and/or laccase. Optionally in any of the methods disclosed herein, such as optionally in any of Aspects 1-41, the one or more enzymes comprises tyrosinase. Optionally in any of the methods disclosed herein, such as optionally in any of Aspects 1-41, the enzyme-containing solution comprises the one or more enzymes at a concentration selected from the range of 1 to 1000 U/mL, optionally 1 to 100 U/mL, optionally 10 to 1000 U/mL, optionally 10 to 100 U/mL. Optionally in any of the methods disclosed herein, such as optionally in any of Aspects 1-41, the enzyme-containing solution comprises the one or more enzymes at a concentration selected from the range of 1 nM to 100 µM, optionally 1 nM to 10 µM, optionally 1 nM to 1 µM, optionally 10 nM to 10 µM.

Optionally in any of the methods disclosed herein, such as optionally in any of Aspects 1-41, the solution is a solution of monoethanolamine or a derivative thereof having a concentration less than or equal to 6% (w/v). Optionally in any of the methods disclosed herein, such as optionally in any of Aspects 1-41, the solution comprises monoethanolamine or a derivative thereof having a concentration less than or equal to 6% (w/v). Optionally in any of the methods disclosed herein, such as optionally in any of Aspects 1-41, the solution comprises monoethanolamine or a derivative thereof having a concentration selected over the range of 1% to 3% (w/v). Optionally in any of the methods disclosed herein, such as optionally in any of Aspects 1-41, the solution comprises monoethanolamine or a derivative thereof having a concentration selected over the range of 1% to 6% (w/v).

Optionally in any of the methods disclosed herein, such as optionally in any of Aspects 1-41, the concentration of the artificial melanin precursors is greater than or equal to 0.1 mg mL$^{-1}$, optionally greater than or equal to 0.3 mg mL$^{-1}$, greater than or equal to 0.5 mg mL$^{-1}$, greater than or equal to 0.8 mg mL$^{-1}$, greater than or equal to 1 mg mL$^{-1}$, optionally selected from the range of 0.1 mg mL$^{-1}$ to 100 mg mL$^{-1}$, optionally selected from the range of 0.1 mg mL$^{-1}$ to 50 mg mL$^{-1}$, optionally selected from the range of 0.1 mg mL$^{-1}$ to 10 mg mL$^{-1}$. Optionally in any of the methods disclosed herein, such as optionally in any of Aspects 1-41, the concentration of the artificial melanin precursors is selected over the range of 0.1 mg mL$^{-1}$ to a saturated solution (i.e., a solution saturated with the artificial melanin precursors), optionally 0.3 mg mL$^{-1}$ to a saturated solution, optionally 0.5 mg mL$^{-1}$ to a saturated solution, optionally 0.8 mg mL$^{-1}$ to a saturated solution, optionally 0.8 mg mL$^{-1}$ to a saturated solution.

Optionally in any of the methods disclosed herein, such as optionally in any of Aspects 1-41, the oxidizing agent is O, $H_2O_2$, $O_3$, and/or $O_2$. Optionally in any of the methods disclosed herein, such as optionally in any of Aspects 1-41, the oxidizing agent is $O_2$. Optionally in any of the methods disclosed herein, such as optionally in any of Aspects 1-41, the oxidizing agent is present in the ambient atmosphere and the solution is exposed to the ambient atmosphere during the contacting step. Optionally in any of the methods disclosed herein, such as optionally in any of Aspects 1-41, the $O_2$ is from air in contact with the alkaline solution or the enzyme-containing solution, thereby providing a source of $O_2$ to the solution. Optionally in any of the methods disclosed herein, such as optionally in any of Aspects 1-41, the concentration of $O_2$ in the alkaline solution is greater than 0 and up to a saturated solution (i.e., a solution saturated with $O_2$). Optionally in any of the methods disclosed herein, such as optionally in any of Aspects 1-41, the contacting step is further carried out in the presence of $H_2O_2$ provided in the alkaline solution. Optionally in any of the methods disclosed herein, such as optionally in any of Aspects 1-41, the concentration of the $H_2O_2$ is less than or equal to 6% (w/v). Optionally in any of the methods disclosed herein, such as optionally in any of Aspects 1-41, the concentration of the $H_2O_2$ is selected over the range of 0.01% to 6% (w/v).

Optionally in any of the methods disclosed herein, such as optionally in any of Aspects 1-41, the contacting step is carried out in the absence of one or more metal salts. Optionally in any of the methods disclosed herein, such as optionally in any of Aspects 1-41, the contacting step is carried out in the presence of one or more metal salts. Optionally in any of the methods disclosed herein, such as optionally in any of Aspects 1-41, the solution is free of metal salts. Optionally in any of the methods disclosed herein, such as optionally in any of Aspects 1-41, the solution comprises one or more metal salts. Optionally in any of the methods disclosed herein, such as optionally in any of Aspects 1-41, one or more metal salts comprise one or more iron salts and/or one or more copper salts. Optionally in any of the methods disclosed herein, such as optionally in any of Aspects 1-41, a concentration of the one or more metals salts in the solution is less than or equal to 15 mM, optionally less than or equal to 10 mM, optionally less than or equal to 5 mM, optionally less than or equal to 1 mM. Optionally in any of the methods disclosed herein, such as optionally in any of Aspects 1-41, the contacting step is further carried out in the presence of one or more metal salts and $H_2O_2$ provided in the solution, for example, in a non-alkaline solution. Optionally in any of the methods disclosed herein, such as optionally in any of Aspects 1-41, the one or more metal salts are nontoxic. Optionally in any of the methods disclosed herein, such as optionally in any of Aspects 1-41, the metal salt is $CuSO_4$. Optionally in any of the methods disclosed herein, such as optionally in any of Aspects 1-41, the concentration of the $CuSO_4$ is less than or equal to 15 mM, optionally less than or equal to 10 mM, optionally less than or equal to 5 mM, optionally less than or equal to 1 mM. Optionally in any of the methods disclosed herein, such as optionally in any of Aspects 1-41, the concentration of the $CuSO_4$ is less than or equal to 100 mM. Optionally in any of the methods disclosed herein, such as optionally in any of Aspects 1-41, the concentration of the $CuSO_4$ is selected over the range of 1 mM to 15 mM. Optionally in any of the methods disclosed herein, such as optionally in any of Aspects 1-41, the concentration of the $CuSO_4$ is selected over the range of 1 mM to 100 mM. Optionally in any of the methods disclosed herein, such as optionally in any of Aspects 1-41, the concentration of the $H_2O_2$ is selected over the range of 0.01% to 6% (w/v).

The following describes certain embodiments of artificial melanin precursors and melanin materials.

Optionally in any of the methods disclosed herein, such as optionally in any of Aspects 1-41, the artificial melanin precursors are substituted or unsubstituted catechol-based or polyol-based compounds. Optionally in any of the methods disclosed herein, such as optionally in any of Aspects 1-41, the artificial melanin precursors are substituted or unsubstituted dopamine monomers. Optionally in any of the methods disclosed herein, such as optionally in any of Aspects 1-41, the artificial melanin precursors are substituted or unsubstituted: dopamine monomers, 1,8-Dihydroxynaphthalene or its derivative, tyrosine monomers, tyramine monomers, amino acids, phenolamines, catecholamines, or any combination of these. Optionally in any of the methods disclosed herein, such as optionally in any of Aspects 1-41, the artificial melanin precursors are substituted or unsubstituted: dopamine monomers, tyrosine monomers, tyramine monomers, or a combination of these. Optionally in any of the methods disclosed herein, such as optionally in any of Aspects 1-41, the artificial melanin precursors are free of phenol derivatives, resorcinol, and/or paraphenylenediamine. Optionally in any of the methods disclosed herein, such as optionally in any of Aspects 1-41, the dopamine monomers are selected from the group consisting of substituted or unsubstituted: dihydoxydopamine monomers, dihydoxydopamine dimers, dihydoxydopamine oligomers, dioxydopamine monomers, dioxydopamine dimers, dioxydopamine oligomers, dihydroxynapthalene monomers, dihydroxynapthalene dimers, dihydroxynapthalene oligomers, dioxydopamine monomers, dioxydopamine dimers, dioxydopamine oligomers, and any combination of these. Optionally in any of the methods disclosed herein, such as optionally in any of Aspects 1-41, the dopamine monomers are selected from the group consisting of tyrosine and derivatives, phenol and derivatives, resorcinol and derivatives, and any combinations thereof. Optionally in any of the methods disclosed herein, such as optionally in any of Aspects 1-41, the dopamine monomers are selected from the group consisting of phenol, resorcinol, L-DOPA, tyrosine and any combinations thereof. Optionally in any of the methods disclosed herein, such as optionally in any of Aspects 1-41, the dopamine monomers are selected from the group consisting of cysteine derivatives, chalcogenides derivatives, selenocysteine, and any combinations thereof. Optionally in any of the methods disclosed herein, such as optionally in any of Aspects 1-41, the artificial melanin precursors are one or more monomers selected from the group consisting of:

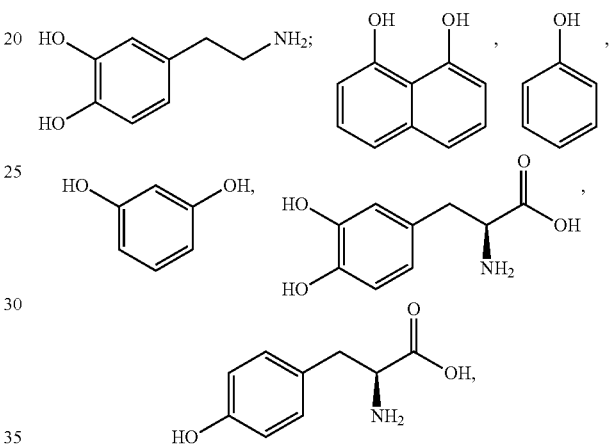

any combinations thereof, and any derivatives thereof. Optionally in any of the methods disclosed herein, such as optionally in any of Aspects 1-41, the artificial melanin precursors are one or more monomers having the formula (FX1):

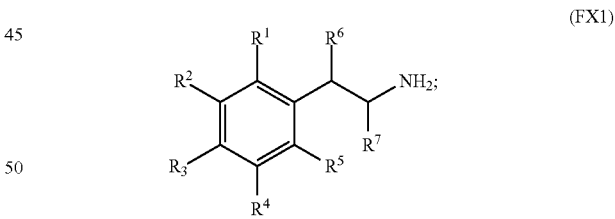

wherein one or more (optionally one, optionally two) of $R^1$-$R^7$ is —OH and wherein each of the other of $R^1$-$R^7$ is a functional group. Optionally, the each of the other of $R^1$-$R^7$ is selected from the group consisting of hydrogen, $C_1$-$C_{10}$ alkyl, $C_3$-$C_{10}$ cycloalkyl, $C_5$-$C_{10}$ aryl, $C_5$-$C_{10}$ heteroaryl, $C_1$-$C_{10}$ acyl, $C_1$-$C_{10}$ hydroxyl, $C_1$-$C_{10}$ alkoxy, $C_2$-$C_{10}$ alkenyl, $C_2$-$C_{10}$ alkynyl, $C_5$-$C_{10}$ alkylaryl, —$CO_2R^{30}$, —$CONR^{31}R^{32}$, —$COR^{33}$, —$NR^{39}R^{40}$, —$NR^{41}COR^{42}$, $C_1$-$C_{10}$ alkyl halide, acrylate, or catechol; wherein each of $R^{30}$-$R^{42}$ is independently hydrogen, $C_1$-$C_{10}$ alkyl or $C_5$-$C_{10}$ aryl. Optionally in any of the methods disclosed herein, such as optionally in any of Aspects 1-41, the artificial melanin precursors are one or more monomers having the formula (FX2):

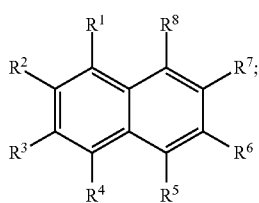

wherein one or more (optionally one, optionally two) of $R^1$-$R^8$ is —OH and wherein each of the other of $R^1$-$R^8$ is a functional group. Optionally, the each of the other of $R^1$-$R^7$ is selected from the group consisting of hydrogen, $C_1$-$C_{10}$ alkyl, $C_3$-$C_{10}$ cycloalkyl, $C_5$-$C_{10}$ aryl, $C_5$-$C_{10}$ heteroaryl, $C_1$-$C_{10}$ acyl, $C_1$-$C_{10}$ hydroxyl, $C_1$-$C_{10}$ alkoxy, $C_2$-$C_{10}$ alkenyl, $C_2$-$C_{10}$ alkynyl, $C_5$-$C_{10}$ alkylaryl, —$CO_2R^{30}$, —$CONR^{31}R^{32}$, —$COR^{33}$, —$NR^{39}R^{40}$, —$NR^{41}COR^{42}$, $C_1$-$C_{10}$ alkyl halide, acrylate, or catechol; wherein each of $R^{30}$-$R^{42}$ is independently hydrogen, $C_1$-$C_{10}$ alkyl or $C_5$-$C_{10}$ aryl. Optionally in any of the methods disclosed herein, such as optionally in any of Aspects 1-41, at least a portion of the artificial melanin precursors have one or more thiol-reactive moieties. Optionally in any of the methods disclosed herein, such as optionally in any of Aspects 1-41, the thiol-reactive moieties are one or more groups selected from the group consisting of a thiol, maleimide, pyridyl disulfide-based compound, alkene, alkyl halide and any combinations thereof. Optionally in any of the methods disclosed herein, such as optionally in any of Aspects 1-41, the artificial melanin material comprises a polymerization product of the artificial melanin precursors. Optionally in any of the methods disclosed herein, such as optionally in any of Aspects 1-41, for example, artificial melanin precursors are one or more monomers having the formula (FX1) or (FX2), wherein one or more of $R^1$-$R^8$ is a thiol-reactive moiety, such as a thiol, maleimide, pyridyl disulfide-based compound, alkene, alkyl halide and any combinations thereof.

Optionally in any of the methods disclosed herein, such as optionally in any of Aspects 1-41, the artificial melanin material comprises artificial melanin nanoparticles, artificial melanin films, artificial melanin flakes, or any combination of these. Optionally in any of the methods disclosed herein, such as optionally in any of Aspects 1-41, the artificial melanin material comprises artificial melanin nanoparticles. Optionally in any of the methods disclosed herein, such as optionally in any of Aspects 1-41, the melanin nanoparticles form a coating on the hair, for example, when the contacting step is carried out at temperatures greater than 30° C. in alkaline solution in the presence of air, for example, wherein the oxidant is $O_2$ in the solution. Optionally in any of the methods disclosed herein, such as optionally in any of Aspects 1-41, the coating is characterized by nanostructures having size domains ranging from 5 nm to 500 nm. Optionally in any of the methods disclosed herein, such as optionally in any of Aspects 1-41, the coating is characterized by nanostructures having a peak size ranging from 5 nm to 500 nm. Optionally in any of the methods disclosed herein, such as optionally in any of Aspects 1-41, the artificial melanin material form a film on the hair, for example, when the contacting step is carried out in the presence of $CUSO_4$ and $H_2O_2$.

The following describes various embodiments for treating hair, according to certain embodiments of methods and materials disclosed herein.

Optionally in any of the methods disclosed herein, such as optionally in any of Aspects 1-41, the temperature is 35 to 45° C. and: (a) the hair is originally a blond color, the alkaline solution is 1% to 6% (w/v) ammonia solution, wherein upon the contacting step the hair changes to a dark brown color; or (b) the hair is originally a blond color, the alkaline solution is 0.01-0.1 N sodium hydroxide solution, wherein upon the contacting step the hair changes to a dark brown color; or (c) the hair is originally a blond color, wherein the contacting step is further carried out in the presence of $CuSO_4$ having a concentration selected over the range of 1 mM to 15 mM and $H_2O_2$ having a concentration of 0.025% to 0.07% (w/v), wherein upon the contacting step the hair changes to a dark brown color; or (d) the hair is originally a blond color, the alkaline solution is 1 to 50 mM tris(hydroxymethyl)aminomethane buffer solution, wherein upon the contacting step the hair changes to a dark grey or light brown color; or (e) the hair is originally a blond color, wherein the contacting step is further carried out in the presence of $CuSO_4$ having a concentration selected over the range of 1 mM to 15 mM and $H_2O_2$ having a concentration of 0.025% to 0.07% (w/v), wherein upon the contacting step the hair changes to a dark brown color; or (f) the hair is originally a blond color, wherein the contacting step is further carried out in the presence of $CuSO_4$ having a concentration selected over the range of 1 mM to 15 mM and $H_2O_2$ having a concentration of 0.1% to 0.2% (w/v), wherein upon the contacting step the hair changes to a dark brown color; or (g) the hair is originally a blond color, wherein the contacting step is further carried out in the presence of $CuSO_4$ having a concentration selected over the range of 1 mM to 15 mM and $H_2O_2$ having a concentration of 0.2% to 0.4% (w/v), wherein upon the contacting step the hair changes to a brown color with shades of red; or (h) the hair is originally a blond color, wherein the contacting step is further carried out in the presence of $CuSO_4$ having a concentration selected over the range of 1 mM to 15 mM and $H_2O_2$ having a concentration of 2% to 4% (w/v), wherein upon the contacting step the hair changes to an orange color; (i) the hair is originally a blond color, the alkaline solution is 1% to 4% (w/v) ammonia solution and wherein the contacting step is further carried out in the presence of $H_2O_2$ having a concentration of 0.1% to 0.2% (w/v), wherein upon the contacting step the hair changes to a brown color; or (j) the hair is originally a blond color, the alkaline solution is 1% to 4% (w/v) ammonia solution and wherein the contacting step is further carried out in the presence of $H_2O_2$ having a concentration of 0.2% to 0.4% (w/v), wherein upon the contacting step the hair changes to a brown color with orange shades; or (k) the hair is originally a blond color, the alkaline solution is 1% to 4% (w/v) ammonia solution and wherein the contacting step is further carried out in the presence of $H_2O_2$ having a concentration of 2% to 4% (w/v), wherein upon the contacting step the hair changes to a bright blond color; or (l) the hair is originally a brown color, the alkaline solution is 1% to 3% (w/v) ammonia solution, wherein upon the contacting step the hair changes to a dark brown color; or (m) the hair is originally a red color, the alkaline solution is 1% to 3% (w/v) ammonia solution, wherein upon the contacting step the hair changes to a dark brown color with shades of red; or (n) the hair is originally a grey color, the alkaline solution is 1% to 3% (w/v) ammonia solution, wherein upon the contacting step the hair changes to a dark brown color; or (o) the hair is originally a grey color, the alkaline solution is 1% to 3% by wt ammonia solution and wherein the contacting step is further carried out in the presence of $H_2O_2$ having a concentration of 0.1% to 0.2% (w/v), wherein upon the contacting step the hair changes to a dark brown color with shades of red.

According to certain embodiments, the methods can be described as including in situ formation of artificial melanin materials and deposition on to the hair and/or update into the hair. Optionally in any of the methods disclosed herein, such as optionally in any of Aspects 1-41, a method of treating hair of a subject with an artificial melanin material comprises: contacting in an alkaline solution artificial melanin precursors with an oxidizing agent at a temperature greater than or equal to 30° C. in the presence of the hair of the subject to form the artificial melanin material; wherein at least a portion of the artificial melanin precursors have one or more thiol-reactive moieties; and wherein the artificial melanin material associates with the hair of the subject, thereby treating the hair of the subject. Optionally in any of the methods disclosed herein, such as optionally in any of Aspects 1-41, for example, the method is carried out in 2 steps: (i) first step, mixing the hair with the artificial melanin precursors (and other solution components) at room temperature and (ii) second step—raising the temperature so as to provide for oxidation and formation of the artificial melanin materials at the higher temperature.

According to certain embodiments, the methods can be described as including ex situ formation and deposition. Optionally in any of the methods disclosed herein, such as optionally in any of Aspects 1-41, a method of treating hair of a subject with an artificial melanin material comprises: contacting in an alkaline solution the hair of the subject with the artificial melanin material having thiol-reactive moieties; wherein the artificial melanin material associates with the hair of the subject, thereby treating the hair of the subject. Optionally in any of the methods disclosed herein, such as optionally in any of Aspects 1-41, the thiol-reactive moieties are one or more groups selected from the group consisting of a thiol, maleimide, pyridyl disulfide-based compound, alkene, alkyl halide and any combinations thereof.

Optionally in any of the methods disclosed herein, such as optionally in any of Aspects 1-41, the contacting step is carried out in the absence of a metal chelating agent. Optionally in any of the methods disclosed herein, such as optionally in any of Aspects 1-41, the contacting step is carried out in the absence of a strong oxidizing condition. Optionally in any of the methods disclosed herein, such as optionally in any of Aspects 1-41, the contacting step is carried out in the absence of sodium periodate.

A variety of materials are disclosed herein for dying hair, which are compatible with methods disclosed herein. Aspects of the invention include a composition of matter comprises the hair of the subject treated with the artificial melanin material generated by any of the methods.

Aspects of the invention include a composition of matter comprises hair of a subject having a coating of artificial melanin nanoparticles, wherein the coating of artificial melanin nanoparticles is characterized by nanostructures having size domains ranging from 5 nm to 500 nm; wherein the artificial melanin nanoparticles associate with the hair of the subject.

Aspects of the invention include an artificial melanin material comprises a polymerization product of artificial melanin precursors at least a portion of which having one or more thiol-reactive moieties.

Optionally, an artificial melanin material is produced by a method comprising: contacting in an alkaline solution artificial melanin precursors with an oxidizing agent at a temperature greater than or equal to 18° C. in the presence of the hair of the subject to form the artificial melanin material; wherein the artificial melanin material associates with the hair of the subject, thereby treating the hair of the subject.

Optionally, an artificial melanin material is produced by a method comprising: contacting in an alkaline solution the hair of the subject with the artificial melanin material having thiol-reactive moieties; wherein the artificial melanin material associates with the hair of the subject, thereby treating the hair of the subject.

Optionally, such as optionally in any of Aspects 1-47, in any method, composition, formulation, and material disclosed herein, the thiol-reactive moieties are one or more groups selected from the group consisting of a thiol, maleimide, pyridyl disulfide-based compound, alkene, alkyl halide and any combinations thereof.

Optionally, such as optionally in any of Aspects 1-47, in any method, composition, formulation, and material disclosed herein, the artificial melanin material comprises artificial melanin nanoparticles. Optionally, such as optionally in any of Aspects 1-47, in any method, composition, formulation, and material disclosed herein, the solution is free of artificial melanin precursors or monomers.

Optionally, the one or more thiol-reactive moieties are one or more groups selected from the group consisting of a thiol, maleimide, pyridyl disulfide-based compound, alkene, alkyl halide and any combinations thereof. Optionally, such as optionally in any of Aspects 1-47, the one or more enzymes comprises one or more oxidoreductase enzymes. Optionally, such as optionally in any of Aspects 1-47, the one or more enzymes comprises tyrosinase and/or laccase. Optionally, the contacting step is carried out in the absence of a metal chelating agent. Optionally, the said contacting step is carried out in the absence of a strong oxidizing condition. Optionally, the contacting step is carried out in the absence of sodium periodate. Optionally, the contacting step does not change the mechanical properties of the hair of said subject. Optionally, such as optionally in any of Aspects 1-47, the artificial melanin material comprises artificial melanin nanoparticles. Optionally, the solution is free of artificial melanin precursors or monomers. Optionally, such as optionally in any of Aspects 1-47, the solution has a pH selected from the range of 4 to 10.

Optionally, such as optionally in any of Aspects 1-47, methods disclosed herein include treatment of hair under room temperature conditions. Optionally, such as optionally in any of Aspects 1-47, a method of treating hair of a subject with an artificial melanin material comprises: contacting in a solution artificial melanin precursors with an oxidizing agent at a temperature greater than or equal to 18° C. in the presence of the hair of the subject to form the artificial melanin material; wherein the artificial melanin material associates with the hair of the subject, thereby treating the hair of the subject; wherein the hair is originally a blond color, wherein the contacting step is further carried out in the presence of $CuSO_4$ having a concentration selected over the range of 1 mM to 15 mM and $H_2O_2$ having a concentration of 0.025% to 0.07% by weight, wherein upon the contacting step the hair changes to a dark brown color; or the hair is originally a blond color, wherein the contacting step is further carried out in the presence of $CuSO_4$ having a concentration selected over the range of 1 mM to 15 mM and $H_2O_2$ having a concentration of 0.1% to 0.2% by weight, wherein upon the contacting step the hair changes to a dark brown color; or the hair is originally a blond color, wherein the contacting step is further carried out in the presence of $CuSO_4$ having a concentration selected over the range of 1 mM to 15 mM and $H_2O_2$ having a concentration of 0.2% to 0.4% by weight, wherein upon the contacting step the hair changes to a brown color with shades of red; or the hair is originally a blond color, wherein the contacting step is further carried out in the presence of $CuSO_4$ having a concentration selected over the range of 1 mM to 15 mM and $H_2O_2$ having a concentration of 2% to 4% by weight, wherein upon the contacting step the hair changes to a dark orange color; the hair is originally a blond color, the alkaline solution is 1% to 4% by wt ammonia solution and wherein the contacting step is further carried out in the presence of $H_2O_2$ having a concentration of 0.1% to 0.2% by weight, wherein upon the contacting step the hair changes to a brown color; or the hair is originally a blond color, the alkaline solution is 1% to 4% by wt ammonia solution and wherein the contacting step is further carried out in the presence of $H_2O_2$ having a concentration of 0.2% to 0.4% by weight, wherein upon the contacting step the hair changes to a brown color with orange shades; or the hair is originally a blond color, the alkaline solution is 1% to 4% by wt ammonia solution and wherein the contacting step is further carried out in the presence of $H_2O_2$ having a concentration of 2% to 4% by weight, wherein upon the contacting step the hair changes to a bright blond color.

Aspects of the invention include a method, composition and/or material is provided for changing the color of the hair of said subject. Aspects of the invention include a method, composition and/or material for darkening the color of the hair of said subject. Aspects of the invention include a method, composition and/or material for restoring the color of the hair of said subject to its natural color. Aspects of the invention include a method, composition and/or material for the coloring of the eyebrows of said subject. Aspects of the invention also include a solution for treating hair or changing color of hair, the solution being according to any embodiment or any combination of embodiments disclosed herein. Aspects of the invention also include a formulation for treating hair or changing color of hair, the formulation comprising a solution according to any embodiment or any combination of embodiments disclosed herein.

Also provided herein are methods and associated formulations for hair treatment utilizing artificial melanin precursors and one or more amine compounds. In aspects, the one or more amine compounds facilitate alkaline conditions during the hair treatment, while being more tolerable to the hair, subject, and/or administrator (e.g., hair stylist; (smell, allergies, etc.) compared to other conventional alkaline agents.

Optionally, such as optionally in any of Aspects 1-47, the solution comprises one or more amine compounds, wherein at least one of the one or more amine compounds is characterized by: (i) having an alpha carbon that is a secondary or tertiary carbon; (ii) a molecule weight less than (optionally, less than or equal to) 150 g/mol; (iii) a pKa greater than (optionally, greater than or equal to) 8; (iv) having at least one hydroxyl group; and (v) being miscible in water; and wherein said artificial melanin material associates with said hair of said subject, thereby treating the hair of said subject.

Optionally, such as optionally in any of Aspects 1-47, the solution comprises one or more amine compounds, wherein at least one of the one or more amine compounds is characterized by formula FX1:

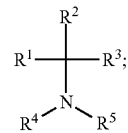

wherein: each of $R^1$, $R^2$, and $R^3$, $R^4$, and $R^5$ is independently a functional group having C, O, H, or any combination of these, with the proviso that no more than one of $R^1$, $R^2$, and $R^3$ is H; wherein the at least one of the one or more amine compounds is further characterized by: (i) having an alpha carbon that is a secondary or tertiary carbon; (ii) a molecule weight less than (optionally, less than or equal to) 150 g/mol; (iii) a pKa greater than (optionally, greater than or equal to) 8; (iv) having at least one hydroxyl group; and (v) being miscible in water; and wherein said artificial melanin material associates with said hair of said subject, thereby treating the hair of said subject. Optionally in any method and formulation herein, each of $R^1$, $R^2$, and $R^3$, $R^4$, and $R^5$ is independently a functional group consisting of C, O, H, or any combination of these. Optionally in any method and formulation herein, each of $R^1$, $R^2$, and $R^3$ is independently selected from the group consisting of H, $CH_3$, OH, $[CH_2]_xOH$, and any combination thereof, with the proviso that no more than one of $R^1$, $R^2$, and $R^3$ is H; each of $R^4$ and $R^5$ is independently selected from the group consisting of H, $CH_3$, $[CH_2]_yOH$, and any combination thereof; and each of x and y is independently an integer selected from the range of 1 to 3. Optionally in any method and formulation herein, each of $R^1$, $R^2$, and $R^3$ is independently selected from the group consisting of H, $CH_3$, OH, $[CH_2]_xOH$, $[CH_2]_zCH_3$, and any combination thereof, with the proviso that no more than one of $R^1$, $R^2$, and $R^3$ is H; each of $R^4$ and $R^5$ is independently selected from the group consisting of H, $CH_3$, $[CH_2]_yOH$, $[CH_2]_mCH_3$, and any combination thereof; and each of x, y, z, and m is independently an integer selected from the range of 1 to 3. Optionally in any method and formulation herein, at least one of $R^1$, $R^2$, and $R^3$ is not $CH_2OH$.

Optionally in any method and formulation herein, at least one of the one or more amine compounds is characterized by having a primary amine group. Optionally in any method and formulation herein, the one or more amine compounds are other than monoethanolamine and tris(hydroxymethyl)aminomethane. Optionally in any method and formulation herein, each of the one or more amine compounds is characterized by formula FX1:

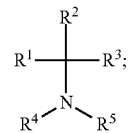

wherein: each of $R^1$, $R^2$, and $R^3$, $R^4$, and $R^5$ is independently a functional group having C, O, H, or any combination of these, with the proviso that no more than one of $R^1$, $R^2$, and $R^3$ is H; and each of the one or more amine compounds is further characterized by: (a) having an alpha carbon that is a secondary or tertiary carbon; (b) a molecule weight less than 150 g/mol; (c) a pKa greater than 8; (d) having at least one hydroxyl group; and (e) being miscible in water. Optionally in any method and formulation herein, each of $R^1$, $R^2$, and $R^3$, $R^4$, and $R^5$ is independently a functional group consisting of C, O, H, or any combination of these. Optionally in any method and formulation herein, each of $R^1$, $R^2$, and $R^3$ is independently selected from the group consisting of H, $CH_3$, OH, $[CH_2]_xOH$, and any combination thereof, with the proviso that no more than one of $R^1$, $R^2$, and $R^3$ is H; each of $R^4$ and $R^5$ is independently selected from the group consisting of H, $CH_3$, $[CH_2]_yOH$, and any combination thereof; and each of x and y is independently an integer selected from the range of 1 to 3. Optionally in any method and formulation herein, each of $R^1$, $R^2$, and $R^3$ is independently selected from the group consisting of H, $CH_3$, OH, $[CH_2]_xOH$, $[CH_2]_zCH_3$, and any combination thereof, with the proviso that no more than one of $R^1$, $R^2$, and $R^3$ is H; each of $R^4$ and $R^5$ is independently selected from the group consisting of H, $CH_3$, $[CH_2]_yOH$, $[CH_2]_mCH_3$, and any combination thereof; and each of x, y, z, and m is independently an integer selected from the range of 1 to 3. Optionally in any method and formulation herein, at least one of $R^1$, $R^2$, and $R^3$ is not $CH_2OH$.

Optionally in any method and formulation herein, each of the one or more amine compounds is selected from the group consisting of aminomethyl proponal, aminopropanol, dimethylaminomethyl propanol, aminomethyl propanediol, tromomethane any combination of these, and any derivative of these.

Optionally in any method and formulation herein, each of the one or more amine compounds is characterized by formula FX2a, FX2b, FX2c, FX2d, or FX2e:

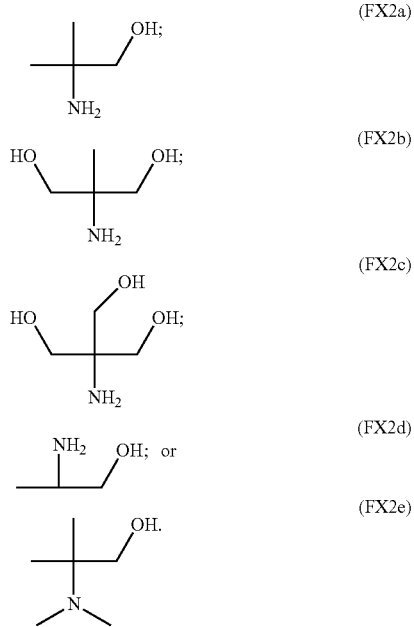

Optionally in any method and formulation herein, each of the one or more amine compounds is characterized by formula FX2a, FX2b, FX2d, or FX2e.

Optionally in any method and formulation herein, at least one of the one or more amine compounds is characterized by a molecular weight selected from the range of 35 g/mol to 150 g/mol.

Optionally in any method and formulation herein, the step of contacting in a solution is performed in the presence of two or more of the amine compounds.

Optionally in any method and formulation herein, the step of contacting is performed in the absence of ammonium hydroxide in the solution. Optionally in any method and formulation herein, the step of contacting is performed in the absence of a buffer or alkaline compound provided for increasing pH of the solution other than the one or more amine compounds.

Optionally in any method and formulation herein, the step of contacting is performed at a pH selected from the range of 8.5 to 14. Optionally in any method and formulation herein, the step of contacting is performed at a pH selected from the range of 12 to 13. Optionally in any method and formulation herein, the step of contacting is performed at a pH of 12.5±0.2. Optionally in any method and formulation herein, the solution further comprises one or more other bases or alkaline agents (e.g., other than amine compounds), such as, but not limited to, ammonium hydroxide, sodium hydroxide, potassium hydroxide, etc., in order to obtain a useful pH of the solution. Optionally in any method and formulation herein, the step of contacting is performed further in the presence of one or more other bases or alkaline agents, such as, but not limited to, ammonium hydroxide, sodium hydroxide, potassium hydroxide, etc., in order to obtain a useful pH of the solution. Optionally in any method and formulation herein, the solution further comprises one or more metal chelators or metal materials, such as iron or iron-comprising material. Optionally in any method and formulation herein, the solution further comprises an enzyme.

Optionally in any method and formulation herein, the step of contacting is performed at a temperature greater than or equal to 20° C. Optionally in any method and formulation herein, the step of contacting is performed at a temperature greater than or equal to 30° C. Optionally in any method and formulation herein, the step of contacting is performed at a temperature selected from the range of 20° C. to 60° C.

Optionally in any method and formulation herein, the step of contacting comprises forming said artificial melanin material and the step of forming said artificial melanin material comprises covalent bonding between the artificial melanin precursors and tat least a fraction of the one or more amine compounds to form said artificial melanin material. Optionally in any method and formulation herein, the step of forming the artificial melanin material comprises polymerization of the artificial melanin precursors.

Optionally in any method and formulation herein, treating the hair of said subject comprises changing hair color of the subject's hair from an initial hair color to a final hair color as a result of the contacting step; and wherein the method further comprises a step of selecting the one or more amine compounds based on a desired final hair color and based on an effect of the one or more amine compounds on the final hair color.

Optionally in any method and formulation herein, treating the hair of said subject comprises changing hair color of the subject's hair from an initial hair color to a final hair color as a result of the contacting step; and wherein: the initial hair color is characterized as blond and the final hair color is characterized as brown or black; or the initial hair color is characterized as gray and the final hair color is characterized as brown.

Optionally in any method and formulation herein, during the step of contacting the solution comprises a total concentration of the one or more amine compounds selected from the range of 0.01 to 15 M. Optionally in any method and formulation herein, during the step of contacting the solution comprises a total concentration of the one or more amine compounds selected to result in a pH of the solution being selected from the range of 8.5 to 14. Optionally in any method and formulation herein, during the step of contacting the solution comprises a total concentration of the artificial melanin precursors is selected from the range of 0.5 to 100 mg/mL.

Optionally in any method and formulation herein, contacting the artificial melanin precursors with the oxidizing agent in the presence of one or more amine compounds and the hair of said subject is performed for a time selected from the range of 30 minutes to 5 hours.

Optionally in any method and formulation herein, the solution is an aqueous solution.

Optionally in any method and formulation herein, the artificial melanin precursors are substituted or unsubstituted: dopamine monomers, 1,8-dihydroxynaphthalene or its derivative, tyrosine monomers, tyramine monomers, amino acids, phenolamines, catecholamines, or any combination of these. Optionally in any method and formulation herein, the artificial melanin precursors are any artificial melanin precursors or any combination of artificial melanin precursors described in International Patent Pub. WO2021/096692 (Gianneschi, et al.; International Patent App. No. PCT/US2020/057939), which is incorporated herein by reference in its entirety.

Optionally in any method and formulation herein, the solution further comprises a metal chelating agent. Optionally in any method and formulation herein, the solution further comprises one or more enzymes.

Optionally in any method and formulation herein, the oxidizing agent comprises oxygen, sodium periodate, potassium permanganate, ammonium persulfate, or any combination of these.

Optionally in any method and formulation herein, the method comprising a step of washing the subject's hair after the treating step is complete.

Optionally in any method herein, the step of contacting is performed for a time selected from the range of 30 minutes to 5 hours, optionally any time selected from the range of 5 minutes to 5 hours.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

As used herein and in the appended claims, the singular forms "a", "an", and "the" include plural reference unless the context clearly dictates otherwise. Thus, for example, reference to "a cell" includes a plurality of such cells and equivalents thereof known to those skilled in the art. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Certain molecules disclosed herein may contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every material, nanoparticle, dispersion, molecule, formulation, combination of components, or method described or exemplified herein can be used to practice the invention, unless otherwise stated.

Every device, system, formulation, plurality of nanoparticles, combination of components, or methods described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

The term "and/or" is used herein, in the description and in the claims, to refer to a single element alone or any combination of elements from the list in which the term and/or appears.

The term "±" refers to an inclusive range of values, such that "X±Y," wherein each of X and Y is independently a number, refers to an inclusive range of values selected from the range of X−Y to X+Y.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A method of treating hair of a subject with one or more artificial melanin materials, the method comprising:
    contacting, in a viscous solution, one or more artificial melanin precursors with an oxidizing agent in the presence of a solution-thickening agent and the hair of said subject to form said one or more artificial melanin materials;
    wherein said one or more artificial melanin materials associates with said hair of said subject, thereby treating the hair of said subject; and
    wherein the step of contacting comprises applying the viscous solution to the hair and subsequently resting the hair for a time.

2. The method of claim 1, wherein during the step of contacting the viscous solution is characterized by a viscosity selected from the range of 0.5 cP to 500 cP.

3. The method of claim 1, wherein during the step of contacting a concentration of the solution-thickening agent in the viscous solution is selected from the range of 0.5 mg/mL to 10 mg/mL.

4. The method of claim 1, wherein the solution-thickening agent comprises hydrogel and/or a hydrogel precursor.

5. The method of claim 1, wherein the solution-thickening agent is characterized as a polysaccharide comprising repeating saccharide units, each saccharide repeating unit comprising at least one amine group.

6. The method of claim 5, wherein each repeating saccharide unit is a disaccharide.

7. The method of claim 1, wherein the solution-thickening agent is characterized as a glycosaminoglycans.

8. The method of claim 1, wherein the solution-thickening agent comprises hyaluronic acid and/or hydroxyethylcellulose.

9. The method of claim 1, wherein the solution-thickening agent comprises hyaluronic acid or a derivative thereof.

10. The method of claim 1, wherein the solution-thickening agent comprises hyaluronic acid.

11. The method of claim 1, wherein the solution-thickening agent comprises a combination of a plurality of different solution-thickening agents.

12. The method of claim 1, wherein the solution-thickening agent is not chemically associated with the one or more artificial melanin precursors and/or with the one or more artificial melanin materials during and after the step of contacting.

13. The method of claim 1, wherein the treated hair after the step of contacting is dyed directly by the one or more artificial melanin materials.

14. The method of claim 1 comprising a step of preparing the viscous solution having the one or more artificial melanin precursors and the solution-thickening agent prior to the step of contacting.

15. The method of claim 14, wherein the step of preparing comprises combining the one or more artificial melanin precursors, the solution-thickening agent, and one or more alkaline agents and/or one or more enzymes in water.

16. The method of claim 1, wherein the one or more artificial melanin precursors polymerize in the presence of the solution-thickening agent prior to the step of contacting.

17. The method of claim 1, wherein at least a portion of the hair, which is in contact with the viscous solution, is submerged in water or an aqueous solution during at least a portion of the step of resting.

18. The method of claim 1, wherein at least a portion of the hair, which is in contact with the viscous solution, is exposed to humid air having a relative humidity of greater than 30% during at least a portion of the step of resting.

19. The method of claim 1 further comprising removing the viscous solution from the hair after the step of contacting.

20. The method of claim 19, wherein the treated hair comprises the artificial melanin material associated therewith after the viscous solution is removed.

21. The method of claim 1, wherein said one or more artificial melanin materials chemically associate with said hair of said subject.

22. The method of claim 1, wherein said one or more artificial melanin materials associate directly with the hair.

23. The method of claim 1, wherein the association between said one or more artificial melanin materials and the hair comprises chemical bonding.

24. The method of claim 1, wherein the one or more artificial melanin precursors comprise substituted or unsubstituted: dopamine monomers, 1,8-dihydroxynaphthalene or its derivative, tyrosine monomers, tyramine monomers, amino acids, phenolamines, catecholamines, or any combination of these.

25. The method of claim 1, wherein the viscous solution further comprises polymerized artificial melanin precursors immediately prior to and/or during the step of contacting.

26. The method of claim 1, wherein the step of contacting is performed further in the presence of one or more alkaline agents and/or one or more pH buffers.

27. The method of claim 1, wherein the step of contacting is performed at a pH selected from the range of 8.5 to 14.

28. The method of claim 1, wherein the step of contacting is performed at a temperature greater than or equal to 20° C.

29. The method of claim 1, wherein the step of contacting is performed at a temperature greater than or equal to 30° C.

30. The method of claim 1, wherein during the step of contacting the viscous solution comprises a total concentration of the one or more artificial melanin precursors selected from the range of 0.5 to 100 mg/mL.

31. The method of claim 1, wherein the viscous solution further comprises a metal chelating agent.

32. The method of claim 1, wherein the viscous solution further comprises one or more enzymes.

33. The method of claim 1, wherein the oxidizing agent comprises oxygen, sodium periodate, potassium permanganate, ammonium persulfate, or any combination of these.

34. The method of claim 1, wherein the one or more artificial melanin precursors are not bound to, conjugated to, attached to, coated by, encompassed by, or otherwise chemically associated with a natural or biological proteinaceous matrix, component, or lipid.

35. The method of claim 1, wherein the one or more artificial melanin materials are in the form of nanoparticles associated with the hair.

36. The method of claim 1, wherein at least a portion of the one or more artificial melanin precursors comprise one or more thiol-reactive moieties.

37. The method of claim 1, wherein the one or more artificial melanin materials comprise a polymerization product of the one or more artificial melanin precursors at least a portion of which having one or more thiol-reactive moieties.

38. A composition of matter comprising the hair of said subject treated with said artificial melanin material generated by the method of claim 1.

39. A composition of matter comprising hair of a subject having a coating of artificial melanin nanoparticles, wherein said coating of artificial melanin nanoparticles is characterized by nanostructures have size domains ranging from 5 nm to 500 nm; wherein said artificial melanin nanoparticles associate with said hair of said subject.

* * * * *